US009977008B2

(12) United States Patent
England et al.

(10) Patent No.: US 9,977,008 B2
(45) Date of Patent: May 22, 2018

(54) METHOD AND APPARATUS FOR ANALYZING ANOMALIES IN CONCRETE STRUCTURES

(71) Applicant: FUGRO USA LAND, INC., Gainesville, FL (US)

(72) Inventors: Melvin Gerrard England, Middlesex (GB); Paul Frederick Cheesman, Chatham (GB)

(73) Assignee: FUGRO USA LAND, INC., Gainesville, FL (US)

( * ) Notice: Subject to any disclaimer, the term of this patent is extended or adjusted under 35 U.S.C. 154(b) by 289 days.

(21) Appl. No.: 14/673,541

(22) Filed: Mar. 30, 2015

(65) Prior Publication Data
US 2015/0276702 A1    Oct. 1, 2015

Related U.S. Application Data

(60) Provisional application No. 61/971,963, filed on Mar. 28, 2014.

(51) Int. Cl.
*G01N 33/38* (2006.01)
*E02D 33/00* (2006.01)
(Continued)

(52) U.S. Cl.
CPC ............. *G01N 33/383* (2013.01); *E02D 5/34* (2013.01); *E02D 33/00* (2013.01); *G01K 1/026* (2013.01);
(Continued)

(58) Field of Classification Search
CPC ........ G01N 33/383; G01N 25/72; E02D 5/34; E02D 33/00; G01K 1/026; G01K 13/10; G01K 2213/00
See application file for complete search history.

(56) References Cited

U.S. PATENT DOCUMENTS 3,659,077 A * 4/1972 Olson ..................... H05B 3/00
                                                          219/213
4,715,726 A * 12/1987 Tsuruta ................ G01N 33/383
                                                          374/102
(Continued)

OTHER PUBLICATIONS

Sellountou, E.A., "Thermal Integrity Profiling: A Recent Technological Advancement in Integrity Evaluation of Concrete Piles," *Proceedings from the First International Conference Seminar on Deep Foundations*, Santa Cruz, Bolivia, Apr. 1, 2013, pp. 1-20. (Retrieved from the internet: URL:http://www.pile.com/refernce/SeminarOnDeepFoundations2013/ThermalIntegrityProfiling.pdf.
(Continued)

*Primary Examiner* — Lisa Caputo
*Assistant Examiner* — Philip Cotey
(74) *Attorney, Agent, or Firm* — Saliwanchik, Lloyd & Eisenschenk

(57) ABSTRACT

Embodiments relate to a method and apparatus for investigating the uniformity of concrete and/or grout. Embodiments can identify the existence of one or more anomalies in the uniformity of concrete and/or grout, and/or determine or estimate the size, shape, type, and/or location of one or more anomalies in the uniformity of concrete and/or grout. Embodiments can utilize a string of temperature measuring sensors placed within one or more access bore(s), such as tube(s), positioned at least partially within the concrete and/or positioned proximate the concrete. The measurements obtained from the temperature measuring sensors can then be used to assist in the identification of existence of, size of, type of, shape of, and/or location of anomalies in the concrete and/or grout.

40 Claims, 17 Drawing Sheets

(51) Int. Cl.
*G01N 25/72* (2006.01)
*E02D 5/34* (2006.01)
*G01K 13/10* (2006.01)
*G01K 1/02* (2006.01)

(52) U.S. Cl.
CPC .............. *G01K 13/10* (2013.01); *G01N 25/72* (2013.01); *G01K 2213/00* (2013.01)

(56) References Cited

U.S. PATENT DOCUMENTS

| | | | | |
|---|---|---|---|---|
| 4,943,930 | A * | 7/1990 | Radjy | G01N 3/02 374/45 |
| 5,041,987 | A * | 8/1991 | Kuwahara | G01N 33/383 340/665 |
| 5,576,494 | A | 11/1996 | Osterberg | |
| 6,116,819 | A | 9/2000 | England | |
| 6,783,273 | B1 | 8/2004 | Mullins et al. | |
| 7,793,720 | B2 * | 9/2010 | Dreher, Jr. | E21B 43/243 166/260 |
| 8,382,369 | B2 | 2/2013 | Piscsalko et al. | |
| 2001/0035053 | A1 * | 11/2001 | McAfee | B28B 7/0094 73/803 |
| 2010/0139915 | A1 * | 6/2010 | Dreher, Jr. | E21B 43/243 166/256 |
| 2011/0200068 | A1 * | 8/2011 | Piscsalko | G01K 1/026 374/152 |
| 2012/0205103 | A1 | 8/2012 | Ravi et al. | |
| 2013/0306308 | A1 * | 11/2013 | Vigneaux | E21B 33/14 166/250.01 |
| 2014/0015155 | A1 * | 1/2014 | Kiest, Jr. | B29C 63/0004 264/40.6 |

OTHER PUBLICATIONS

Search Report and Written Opinion for International Application No. PCT/IB2015/000680.
Mullins, G., "Thermal Integrity Profiling of Drilled Shafts," *DFI Journal*, Dec. 2010, vol. 4, No. 2, pp. 54-64.
Mullins, G. et al., "Thermal Integrity Profiling: An Innovative Technique for Drilled Shafts," *The Journal of Deep Foundations Institute Special Issue: Innovation*, May/Jun. 2012, pp. 51-54.
Mullins, G. et al., "Thermal Integrity Profiler," GRL Engineers, Inc./Pile Dynamics, Inc. Newsletter No. 66, 2011, pp. 1-2.

* cited by examiner

Thermal coupler and conduit pipe

Thermal coupler and conduit pipe

METHOD AND APPARATUS FOR ANALYZING ANOMALIES IN CONCRETE STRUCTURES

CROSS-REFERENCE TO RELATED APPLICATION

The present application claims the benefit of U.S. Provisional Application Ser. No. 61/971,963, filed Mar. 28, 2014, which is hereby incorporated by reference herein in its entirety, including any figures, tables, or drawings.

BACKGROUND OF INVENTION

The installation of deep foundations in the ground often require numerous steps to be effectively completed, and is very technique dependent.

Foundation elements may be constructed by many methods, with each method having its own associated difficulties and limitations with respect to the assessment of the true profile of the excavation and, consequently, the success with which the concrete/grout has been delivered and the shape of the cured material after casting. Assessment of the profile and the integrity of any foundation element can provide the engineer/contractor/owner confidence that the construction of the foundation element meets the requirements of the design of the foundation.

A bored pile or deep foundation is one where a hole is excavated using, for example, a drilling rig with a rotary powered mechanical bucket, auger, or coring barrel, in the case of a piled shaft, or a crane suspended mechanical excavating tool, either hydrofraise (reverse circulation trench cutter) or grab, in the case for a rectangular section wall. To add strength to the foundation element, a steel cage is typically lowered into the excavation and concrete is poured into the bore in a manner in which the steel is cast in place to design level, thus providing a steel reinforced structure. The excavation techniques used take into account the soil types that are being excavated and the water pressures within them. They may be excavated dry, under water, or using bentonite slurry or polymer as a retaining fluid to equalise pressures and to stabilise the ground within the excavation. There may be casing at the top of the excavation to retain any unstable material and in the case of some bored piles, a temporary casing may extend the full length to the bottom of the pile and be removed as the concrete is placed or soon afterwards.

Placement of the concrete may be performed by a tremie pipe, extending to the base of the excavation at the start of concreting and withdrawn as the concrete level rises, or by concrete pump through a pipe in a similar manner. The concrete placement may scour the base of the excavation to dislodge any debris and lift it to the surface by flotation as the concrete level rises. The concrete may be poured either directly from the top or by short pipe in the case of a dry excavation or by a combination of methods dependent on the depth of excavation.

Auger type soil displacement and soil replacement piling techniques, such as continuous flight auger/auger cast and a variety of screw type partial displacement or full displacement piles use a hollow stemmed auger or mandrel to make the pile hole. The concrete or grout is then pumped through the auger or mandrel as it is removed to form the pile. Reinforcement is placed by gravity or by pushing from the top, after the concrete or grout has reached piling platform level.

Driven cast-in-situ piles are performed with a variety of techniques but in general they utilise a steel tube with an expendable shoe to displace the soils leaving an internal void. The tube is filled with concrete which fills the void and as the tube is removed the concrete flows to the outer edges of the shape formed. The reinforcement is either placed in the tube before the concrete is poured, thus leaving it behind as the tube is removed or placed by gravity or pushing from the top after the tube is removed.

The requirement for checking that the concreting procedure has been successfully completed without soil inclusions, voids, honeycombing or other defects is paramount to ensuring good quality construction and suitability of the foundation element for the design purposes. The precise level of the concrete at any time, combined with the delivery rate information, also assists in determining the shape of the excavation as the volume of concrete placed with depth will determine the general profile of the excavation.

Instrumentation on piling rigs used for auger cast methods can give some indication of the cross-sectional area of the bore with depth as concrete/grout flow is monitored during casting (as described in U.S. Pat. No. 6,116,819), but will not typically give details of how the cross-section is finally distributed with depth or deficiencies in the pile formation.

In all types of excavation, the precise positioning of the reinforcement cage generally remains unknown after concrete/grout has been poured.

Another method of deep foundation construction is to form an injection column where grout injected under pressure through a probe tube displaces the soil under or alongside the point of injection. The procedure may also involve mixing the soil with the grout as it is injected or it may be soil mixing with the external addition of grout. Once the injection probe has reached the required depth, pressurised grout is injected as the probe rotates and is extracted forming either a continuous column up to ground level (not necessarily of the same diameter) and reinforcement bars may be placed to strengthen the load bearing capabilities and assist in the attachment of the column to the building foundations. The direction and path of the grout injection is unknown and, thus, the column shape constructed is also unknown. A minimum bearing capability based on the minimum expected column size is typically used in the foundation design, but means of assessment of the geometry of the constructed column do not exist.

A method of assessing the general profile of any deep foundation and the location of the reinforcement steel cage or bars within the foundation profile is then a valuable tool in the quality assurance of the deep foundation construction.

A variety of testing techniques have been developed to assist in the quality assurance of deep foundations so that, once installed, an assessment in terms of reliability, final geometry, and/or integrity (among other things) may be carried out. Anomalies within the structure of deep foundations may be detected by various non-destructive methods with varying degrees of efficiency, cost, ease of use, and success. Cross Hole Sonic Logging (CHSL) as described in ASTM 6760 and Sonic Integrity Testing (SIT) ASTM D5882 and summarised in the following sections a) and b) and "Thermal Integrity Profiling of Drilled Shafts", described by Gray Mullins, DFI Journal, Vol. 4, No. 2 Dec. 2010:

a). The cross hole sonic logging method is performed by sending ultrasonic pulses through the material of the foundation element, usually, concrete from one emitter to one or more receivers generally across a horizontal path inside the reinforced concrete structure and analysing the transit time and signal strength between each pair of water filled tubes. The test requires pre-installed access/reservation tubes of a nominal 38 to 60 mm internal diameter, cast into the pile shaft parallel to one another and to its axis. The number and configuration of the tubes is determined by the size of pile and the test sequence required. This is normally taken as one tube for every 0.25 to 0.35 m of pile diameter but a minimum of three tubes is required in order to provide any worthwhile assessment.

The placement of cross hole sonic logging (CHSL) tubes within a reinforcement cage during deep foundation construction has been a testing method available for many years and a requirement in testing specifications. Until recently, it was one of the few non-destructive testing techniques which can provide an assessment along the full length of the foundation element. The joining of the CHSL tubes at the reinforcement splice levels is difficult and has been an issue of safety for the deep foundation industry with many injuries occurring when the tubes, which are often long and heavy, need to be lifted and connected which can be by welding or screw connection or just push fit and where arms and fingers need to be inserted within the reinforcement cage during connection and installation of each reinforcing cage which carries the CHSL access tubes.

An emitter lowered down one tube transmits a high frequency signal, which is sensed at some time later by the receiver in an adjacent tube generally at the same elevation. The sensors are then moved up the pile shaft in a synchronised manner until the whole shaft has been scanned. The test is repeated for each pair of tubes, allowing for the investigation of variations which might be interpreted as anomalies of varying severity both along the length and for each transit path.

The emitter and receiver are attached to PVC cable which is used to lower the sensors down the access tubes and to determine their depth. Each access tube may have its own depth encoder fitted at the top to allow accurate depth measurements to be recorded for each cable. There are several limitations of the CHSL testing method:
1. The zone of material assessment is limited to the path between access tubes;
2. The test cannot detect any anomalies outside of the reinforcement cage;
3. The access tubes have to be nominally parallel to the pile or shaft axes;
4. The tubes need to be filled with clean water prior to performing the test.
5. The access tubes must be clean internally and fully bonded to the concrete externally. Any debris, grease or joint taping may be misinterpreted as an anomaly in the structure;
6. The method is not suitable for smaller pile/shaft diameters where the percentage of the cross section due to the tubes is high;
7. Joining of the tubes at each cage splice level is difficult, time consuming and presents many safety issues;
8. Leakage of the tubes due to filling with water when the concrete is wet to assist bonding may result in washing of concrete locally around the joints causing the very anomalies the test can detect;
9. No indication of the quality of the concrete at the base is possible;
10. Assessment of concrete quality is limited as transit time changes of 20% may be expected from minor changes in position of the sensors.
11. Cost b). The sonic integrity test (SIT) is carried out by tapping the head of the pile with a small hand held hammer to generate an acoustic wave which spreads from the blow down through the pile. The plane waves generated are then reflected by any changes of acoustic impedance which may be discontinuities within the pile shaft or changes of soil material type and stiffness surrounding the pile shaft and the returning waves are detected by means of an accelerometer located at the pile head.

The depth from which these waves are returned is calculated by assuming the propagation velocity of the wave in the pile concrete. This method is normally referred to as the Sonic Echo method, but has been referred to by lots of other names.

A series of blows are taken and an average of the best blows obtained is used for analysis. Each test result may be plotted to show the velocity at the pile head against time/depth. Amplification of the signal with respect to time/depth may be used to enhance the clarity of the plot (and remove the influence of attenuation along the length of the element). Reflections detected at the pile head from changes of acoustic impedance down the length of the test pile, allow for detection of anomalies in the pile cross section. A change in the pile head velocity can be detected and when assessed against time/depth, can assist identifying from where along the pile shaft the reflection may have originated. The nature and degree of change of impedance at any point is a function of the magnitude of change of pile cross-section, ground conditions and wave propagation velocity (concrete quality).

Any change in the amplitude of the acceleration recorded at pile head, other than the initial hammer blow, can therefore be interpreted to indicate one of the following:
1. The pile toe.
2. A cross-sectional crack.
3. A change in cross-section (necking or bulging). This may be deliberate due to pile construction and/or a consequence of the surrounding soils.
4. Poor concrete. (Major segregation or localised voiding)
5. Soil inclusions.
6. Changes in soil/pile shaft friction.
7. A combination of any of the above factors.

The test is useful for rapid assessment of multiple circular shafts of a relatively short length on a site after the piles have been trimmed to sound concrete. The test is limited by a length to diameter ratio, usually around 20:1 to 30:1 dependent on the soils surrounding the shaft. It is not suitable for large diameter shafts, rectangular sections such as walls or piles that are not of uniform construction such as injection columns or soil mix columns. Major anomalies and horizontal cracks may be detected but minor anomalies are difficult to detect or define and accurately assess.

c). The Thermal Integrity Profiling (TIP) technique addresses some of the issues raised above and the methods employed are described in U.S. Pat. No. 6,783,273 and U.S. Pat. No. 8,382,369 but do not allow for detailed profiling without the placement of additional reservation pipework for probe access or the permanent installation and consequent loss of expensive strings of thermal sensors due to their permanent embedment in the structure.

The objective of thermal integrity profiling is the measurement of distribution of temperature during the curing of the material, several aspects will contribute to the temperature distribution axially and radially: the composition of the mixed materials, can lead to faster/slower times to reach the peak temperature, a lower than expected peak temperature; the background temperature and density of the soil surrounding the foundation element, being part of the heat diffusion path by thermal conductivity.

Fortuitously, the absolute temperature, the maximum temperature achieved, the cause and effect is not of great significance to the assessment that may be made by this thermal profiling method as it is the relative changes, which are significant.

By analysis of the temperature distribution at some instance in time along a line parallel to the axis of the foundation element, localised variations in temperature can be detected as can general trends, which may be indicative of several factors, such as curing speed of the material of the foundation element, the composition of the in situ concrete, density, and the effect the surrounding soil/material has in terms of thermal influence on the zones measured. From variations in temperature distribution along the length or from radially equidistance/symmetrically located measurements, some first level assessment may be made to identify anomalous zones which may require more detailed investigation.

The Thermal Integrity Profiling (TIP) technique, which is performed by assessment of the distribution of temperature within the foundation element during the curing process, may be carried out either by:

1. As described in U.S. Pat. No. 6,783,273, a probe pulled from the bottom of a large diameter tube (normally a cross hole logging tube 50 mm or 60 mm OD or larger) to the top of the foundation element (or vice versa) by means of a tripod arrangement at the head of the access tube with a means of locating the sensor in the centre and fitted with a depth encoder to allow correlation of the temperature measurements with the elevation within the foundation element. The access tubes are normally dry and the probes use thermal imaging techniques requiring a relatively large diameter tube to be pre-installed in the foundation element before concrete placement. The tube is required to be dry for the infrared measurements to be possible and, as the act of pulling the infrared sensor probe in a fluid would produce some turbulence by the probe causing flow of fluid around the sensor, it would affect accurate local temperature measurements of the surrounding concrete/grout. The procedure of measuring the distribution of temperature may be carried out once or several times in the same access tube during the concrete curing process. Several reservation tubes may be installed at different locations parallel to the axis of the foundation element.

2. As described in U.S. Pat. No. 8,382,369, a fixed permanently embedded thermal string may be used in which a series of individual sensors, such as type K thermocouples may be used and attached to the reinforcement of the foundation element prior to casting. Alternative thermal strings may be made up in series using MEMS technology, thus minimizing the number of electrical connection cables required and allowing a plurality of sensors to be deployed that may be read consecutively once the concrete has been cast. The string length may be manufactured, to correspond to the cage length or standard lengths with suitable electrical connections required at the splicing elevations. Alternatively, they may be continuous and manufactured the full length of the multiple section cage and be tied to outside of the reinforcing cage as it is being inserted into the bore.

During initial curing of the concrete, the temperature sensors may be set to record at predetermined time intervals. As the concrete/grout cures the heat of hydration will increase the temperature within the foundation element, reaching a peak and then dropping as the concrete/grout cures. Detailed investigation of the temperature throughout the element may result in identification of anomalous peaks and troughs in the temperature profile. These anomalies may be further interpreted to be the result of potential defects within the foundation element. Changes in the curing rate across the foundation element may indicate the proximity of the temperature strings to the outer wall of the concrete/grout, ingress of alien material within the anticipated envelope of the foundation element, proximity of the sensor to the surrounding bore wall and even be indicative of the surrounding soil conditions.

Embodiments relate to a method and apparatus for identifying and estimating the size and/or location of anomalies in the uniformity of concrete. Specific embodiments can provide information regarding concrete and/or grout used with a piled shaft, barrette, or other load bearing concrete or grout foundation element. Specific concrete and/or grout structures that can be investigated include, for example, foundations, piles, barrettes, or other structures. Specific embodiments can utilize a string of temperature measuring sensors placed within one or more access bore(s), such as tube(s) positioned at least partially within the concrete and/or positioned proximate the concrete. Specific embodiments can utilize tube(s) attached to a reinforcement cage or framework as access bores. A variety of placement methods of the tube(s), or conduit(s), and string may be utilized. In specific embodiments, the tube(s) cast in place or plunged into wet concrete and/or grout during construction. The conduit(s) may be positioned such that longitudinal axis of the conduit(s) follow a variety of paths, such as across and/or around the base of the foundation element. Conduit(s) placed near the base of the foundation element can detect changes in the temperature profile associated with the end bearing material of the base. Significant variations in the temperature in real time, as a result of changes in the localized concrete and/or grout curing temperature due to heat generated by hydration, are affected by the geometry and density of the surrounding materials and these variations in temperature may be due to anomalies within the concrete and/or grout material. The measurements obtained may then be used to assist in the identification of existence of, size of, type of, shape of, and/or location of anomalies in the concrete and/or grout. Specific embodiments can use such information to produce a 3D representation of the temperature variations, which can ease identification of the extent and location of the anomalies.

In a preferred embodiment, the string of thermal sensors can be retrieved from the conduits in which the string is positioned during measurement, such as temperature measurements.

FIGS. 1-22 show a variety of specific embodiments having thermal coupler and conduit pipe (e.g., thermal string positioned within a conduit), and a data reader connected to the thermal strings, described below.

DETAILED DISCLOSURE

Figure 1:
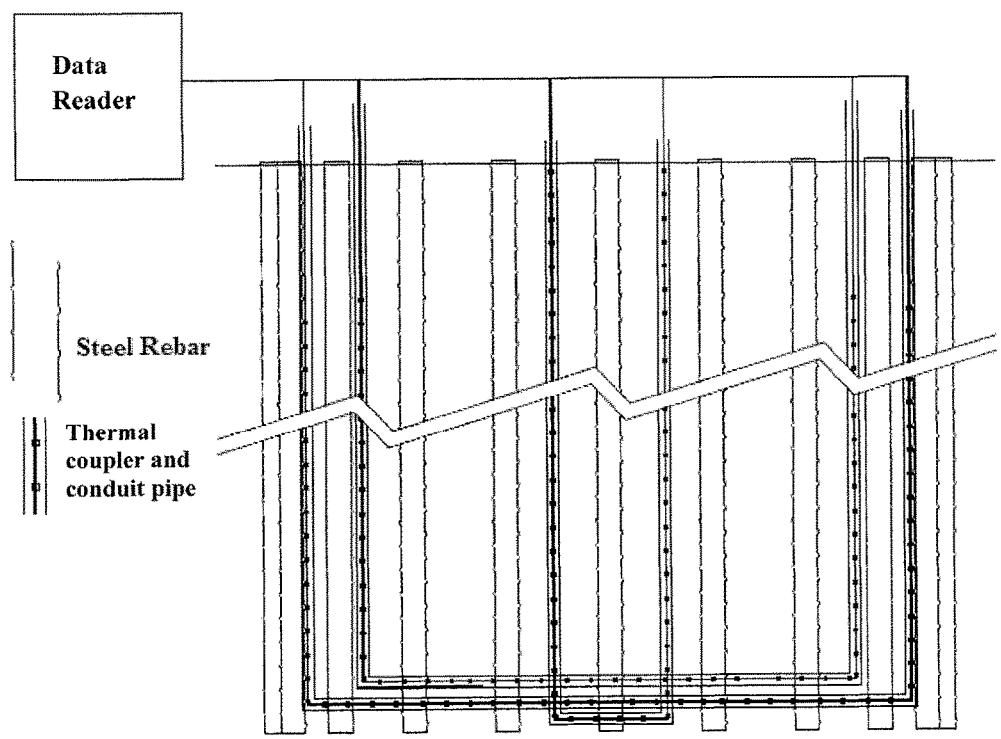
FIG. 1 shows a side view of a cylindrically shaped volume, where the concrete is not shown, showing three U-shaped conduit pipes with thermal coupler(s) within the conduit pipes, steel rebar, and a data reader.

Embodiments relate to a method and apparatus for identifying and estimating the size and/or location of anomalies in the uniformity of concrete. Specific embodiments can provide information regarding concrete and/or grout used with a piled shaft, barrette, or other load bearing concrete or grout foundation element. Specific concrete and/or grout structures that can be investigated include, for example, foundations, piles, barrettes, or other structures. Specific embodiments can utilize a string of temperature measuring sensors placed within one or more access bore(s), such as tube(s) positioned at least partially within the concrete and/or positioned proximate the concrete. Specific embodiments can utilize tube(s) attached to a reinforcement cage or framework as access bores. A variety of placement methods of the tube(s), or conduit(s), and string may be utilized. In specific embodiments, the tube(s) cast in place or plunged into wet concrete and/or grout during construction. The conduit(s) may be positioned such that longitudinal axis of the conduit(s) follow a variety of paths, such as across and/or around the base of the foundation element. Conduit(s) placed near the base of the foundation element can detect changes in the temperature profile associated with the end bearing material of the base. Significant variations in the temperature in real time, as a result of changes in the localized concrete and/or grout curing temperature due to heat generated by hydration, are affected by the geometry and density of the surrounding materials and these variations in temperature may be due to anomalies within the concrete and/or grout material. The measurements obtained may then be used to assist in the identification of existence of, size of, type of, shape of, and/or location of anomalies in the concrete and/or grout. Specific embodiments can use such information to produce a 3D representation of the temperature variations, which can ease identification of the extent and location of the anomalies.

In a preferred embodiment, the string of thermal sensors can be retrieved from the conduits in which the string is positioned during measurement, such as temperature measurements.

An embodiment using a string of thermal sensors that can be retrieved can be implemented by the telltale casings in the concrete structure. In an embodiment, telltale casings (e.g., mechanical extensometers) can be used with an O-cell, which can be used for, for example, bi-directional loading tests of the foundation (as described in U.S. Pat. No. 5,576,494). The telltale casings can be inserted in a pile, such as a test pile, and extend to the bottom, or near the bottom, of the pile. These casings can be cast in the concrete and, in an embodiment, have an internal diameter in the range 12 mm to 18 mm ID. During the load testing, a steel rod can be inserted in the telltale casings and the steel rod can be used as a mechanical link from the end of the pipe (or telltale casing) to a point at which the vertical position of the rod can be measured. During the curing period of the concrete, as these casings are generally empty, embodiments position a string of thermal sensors (which can be referred to as thermal strings) in the casings, allowing the thermal profile along the casing to be measured.

The use of cross hole sonic logging (CHSL) is typically not considered practical for piles with diameters less than 1 m, as the reservation tubes used for CHSL take up such a large proportion of the cross sectional area of the pile. For a pile having a diameter less than 1 meter, in order to stay within an acceptable proportion of cross-sectional area taken up with the reservation tubes, two reservation tubes can be used to house temperature sensors, resulting in test data of limited technical value. Specific embodiments can be used for piles having a circular cross-section through the longitudinal axis with diameters less than 2 meters, less than 1.75 meters, less than 1.5 meters, less than 1.4 meters, less than 1.3 meters, less than 1.2 meters, less than 1.1 meters, and/or less than 1 meter, piles having a rectangular cross-section through the longitudinal axis, where each side is less than 2 meters, less than 1.75 meters, less than 1.5 meters, less than 1.4 meters, less than 1.3 meters, less than 1.2 meters, less than 1.1 meters, and/or less than 1 meter, and/or piles having a cross-sectional area through the longitudinal axis of less than 4 $\pi m^2$, less than 3 $\pi m^2$, less than 2 $\pi m^2$, less than 1.5 $\pi m^2$, less than 1.2 $\pi m^2$, less than 1.1 $\pi m^2$, and/or less than $\pi m^2$. Embodiments using one or more thermal string positioned in at least one conduit, e.g., with cast in situ or precast elements, ground anchors, jet grouting, soil mixing, and/or mini piles can allow the cost of the temperature measurements to be cost effective.

Specific embodiments of the subject invention can include one or more of the following features:
1. Accomplish CHSL without the use of sonic logging access tubes and/or without the associated safety and installation difficulties associated with the CHSL method;

2. Provide a cost effective testing method using temperature sensors, where expendable materials are of low value and/or the temperature sensors can be recovered;
3. Provide a method and apparatus to provide a detailed assessment of the quality of the construction material at the base of a shaft;
4. Assess the possibility of the presence of debris at the base of a foundation structure, footing, or other types of foundation elements that may be profiled;
5. Accurately monitor the concrete level during construction of cast in place piles;
6. A method and apparatus that can provide testing using temperature sensors with respect to piles having a diameter less than 1 meter and/or less than 2 meters; and
7. Protect the thermal sensors from damage from flowing concrete.

A string of temperature sensors, which can be referred to as a thermal string, can include one or more, and preferably at least 2, at least 5, at least 10, at least 20, at least 30, at least 40, and/or at least 50 thermal or temperature measuring devices joined together to make one entity. A thermal string may take a variety of forms, such as electrical cables connecting thermocouples, thermistors, fiber optic, or any other local temperature measuring device or devices. The thermal string can have an elongated form for positioning within a tube, conduit, telltale casing, and/or bore in the concrete, and can have a flexible, semirigid, rigid, segmented, or other form. In specific embodiments, the string can incorporate a continuous wire/rope, such as a steel wire (or other material). The continuous rope/wire can be incorporated into the sting to give the string strength in tension so the string can be extracted successfully. The other portions of the string can be tied to the steel wire so the cabled sensors do not have to carry their own weight, and the string can then be inserted and extracted in the reservation pipe to greater depths. Incorporation of such a continuous wire/rope can allow the use of jointed sensor/cable that had a limitation regarding the force applied at each joint, e.g., not more than 20 kg applied each sensor/cable joint.

The thermal strings may be arranged as discrete sensors in a bundle, with connection to each from outside the tested element, with individual connections to each individual sensor. The thermal strings can also be arranged as a chain of intelligent devices, such as MEMS devices, housed in a miniature casing along with the interface electronics so that many sensors can be placed in series in a manner that allows power delivery, interrogation, and response detection through a number of cable strands, and preferably less than 5 cables (a specific embodiment uses 4 cables). In an embodiment, at least 100, 200, 300, 400, and/or 500 sensors can be used in this way to assemble one or more thermal strings, where the sensors are spaced apart by distances less than 10 mm, less than 50, less than 100, less than 200, less than 300, in the range 10-50, 50-100, 100-200, 200-300, 100-300 mm and/or greater than 300 mm, depending on the size of the foundation element to be profiled and the degree of resolution required. In a specific arrangement, a full thermal string is contained within a conduit having an inner diameter in the range 12-18 mm, less than 60, less than 50, less than 40, less than 30, less than 20, in the range 18-20, 10-12, 14-16, 12-14, 16-18, and/or less than 10 mm. Embodiments can provide data communication via a serial connection. In embodiments where the string is retrievable, the sensors and individual logging units can be self-contained, and the data can be recorded locally for each sensor so that, upon removal, of the thermal string and/or device, the stored data can be captured, and/or uploaded for analysis.

Embodiments can involve constructing a thermal string having one or more of the following features:
1. Using the electrical cable connecting each sensor, which can also be used as a spacer between separate sensors, where the cable forms the interconnecting element for each sensor (suitable for MEMS devices);
2. Electrical multi-cable connection as above where each sensor is directly connected to the display/logger/reader;
3. Fixed rod, where the sensors are attached to the rod, whether it is rigid or flexible, the sensors being connected by 1. or 2. above;
4. Short pieces of rod between the sensors allowing the whole string to be semi-flexible to aid rigidity when pushing the string through a conduit, but allowing flexibility to move around bends in the conduit;
5. An optical fiber glass or plastic string, where the one or more sensor is an integral part of the string, such as an arrangement of one or more gratings.
6. A continuous wire or continuous rope, such as a steel wire (or other material) to which the sensors are attached, incorporated with one of the embodiments 1-5 above.

The thermal string can be constructed for insertion and/or removal from a conduit, has a specific advantage over casting the bare string within a foundation element directly in that it does not need to be ruggedized to withstand the flow of concrete and/or grout around the string. Such ruggedizing can make the string prone to failure. Embodiments configured to be inserted into the conduit before, during, and/or after concreting, and/or removed after testing, can be removed and replaced, for example if a failure to operate correctly is observed.

Several methods of placing thermal strings can be utilized and can be used to assess the thermal profile and/or integrity of a foundation element.

A preferred embodiment is a system employing a retrievable thermal string or strings where the string can be placed in one or more than one conduit independently or in a continuous string. Preferably, during the temperature monitoring, the conduit is filled with a fluid such as water, oil, or other fluid or viscous material or heat conducting material to allow easier placement and retrieval of the string. Pairs of tubes can be joined at the base so that the string can be passed down a first conduit, along a section at or close to the base, and up a second conduit. Preferably, the string can be extending from the first and second conduits at the same time, which can allow tension to be applied to the string to stretch the string to, for example, reduce bunching. Several pairs of tubes may be used, allowing a detailed profile of the foundation element and the base. By use of a single string, or multiple strings connected in series, a single data logger system can be used, either as a stand alone collector for later data retrieval or connected to a computer or other such device to allow for delayed and/or live monitoring in real time, either by direct connection or via modem or remote similar link.

Advantageously, to make a direct mechanical and thermal connection to the inside of the conduit, each sensor may be activated so that the structure of the sensor causes the sensors to be mechanically pushed against and/or positioned against the conduit. This may be achieved by having a small pressuring pipe, separate from the cabling or surrounding the cables and sensors, which connects to a small balloon type arrangement at the location of each of the sensors, conveniently located on the opposite side of the sensor element so the sensor becomes pressed up against the inside of the conduit when inflated. This approach is particularly suited to, but not limited to, situations where fluid is not used within the conduit. In a similar manner, rotation of an eccentric cam may be used to position the sensor.

Figure 2:
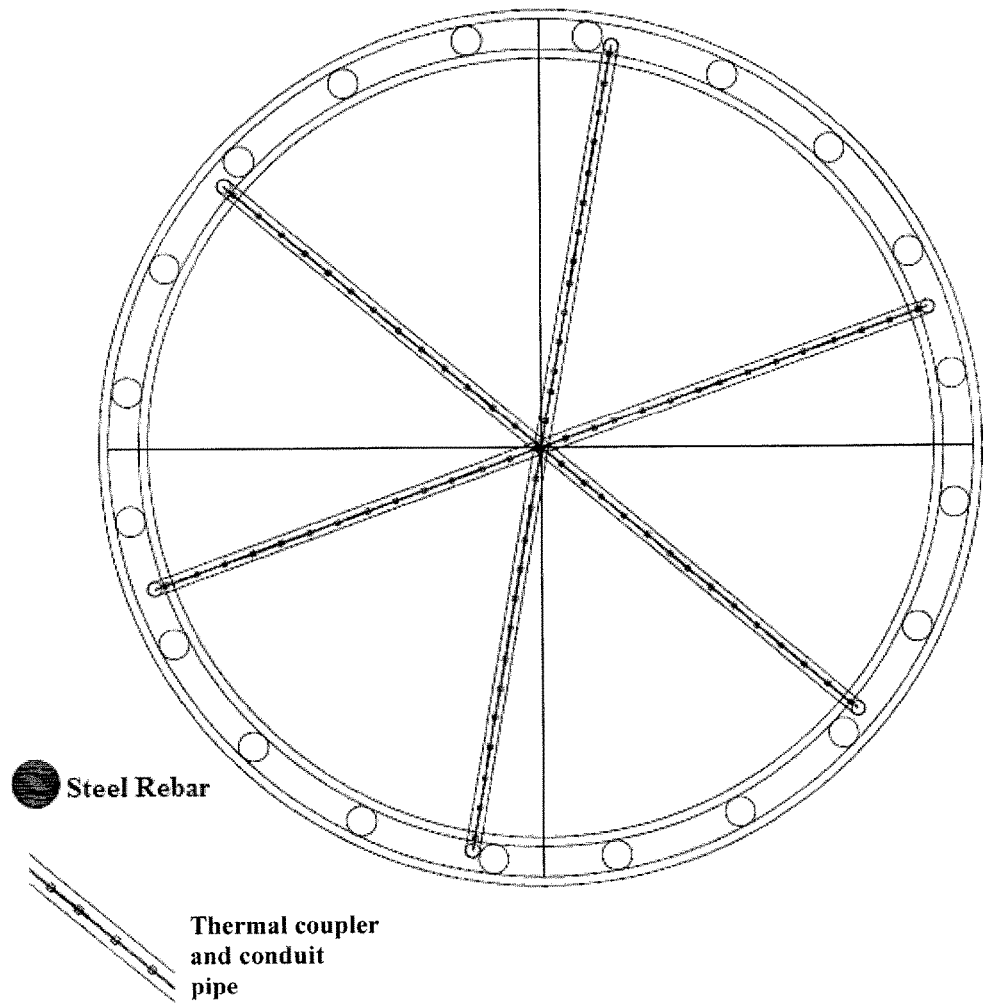
FIG. 2 shows an end view of the embodiment of FIG. 1.
Figure 3:
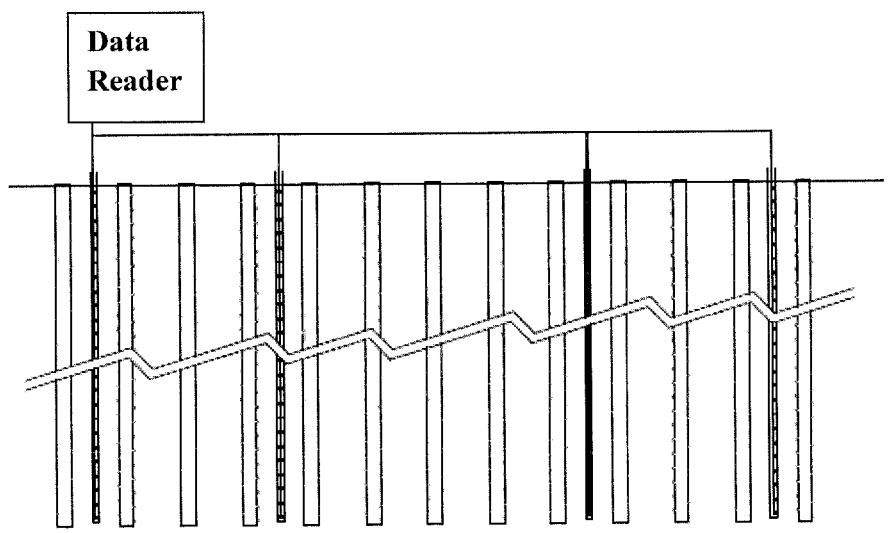
FIG. 3 shows a side view of a rectangular shaped (rectangular cross-section across the longitudinal axis) volume, where the concrete is not shown, showing four U-shaped conduit pipes with thermal coupler(s) within the conduit pipes, steel rebar, and a data reader.
Figure 4:
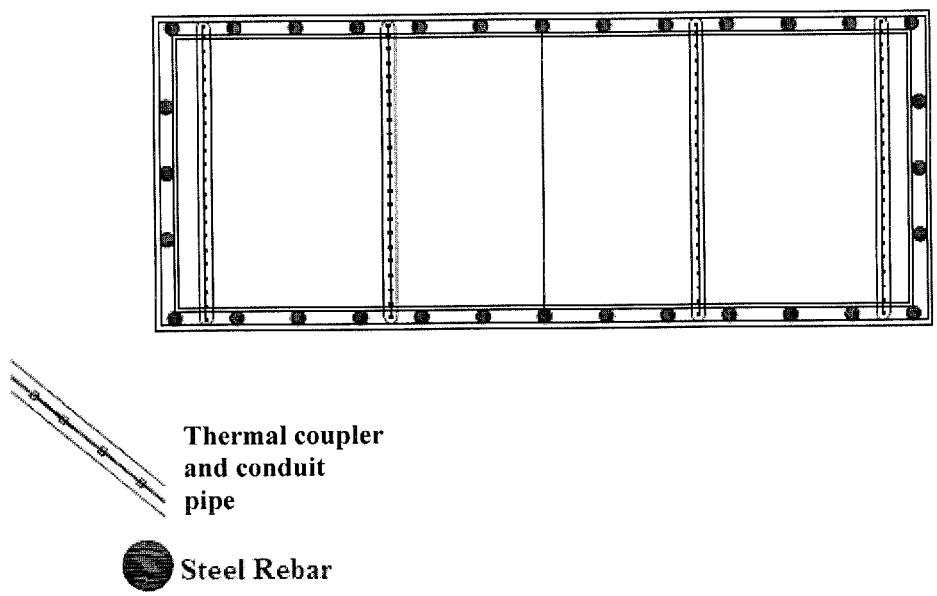
FIG. 4 shows an end view of the embodiment of FIG. 3.
Figure 5:
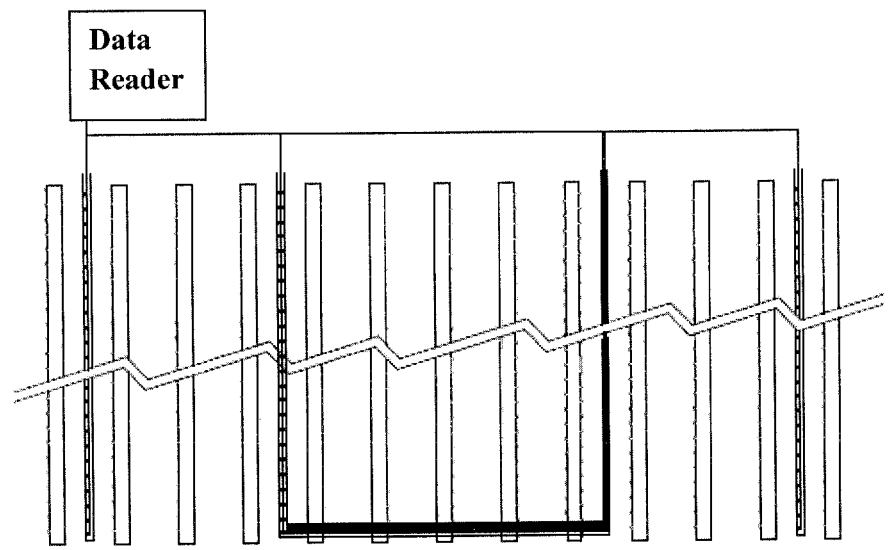
FIG. 5 shows a side view of a rectangular shaped (rectangular cross-section across the longitudinal axis) volume, where the concrete is not shown, showing four U-shaped conduit pipes with thermal coupler(s) within the conduit pipes, steel rebar, and a data reader, where two of the U-shaped conduit pipes cross.
Figure 6:
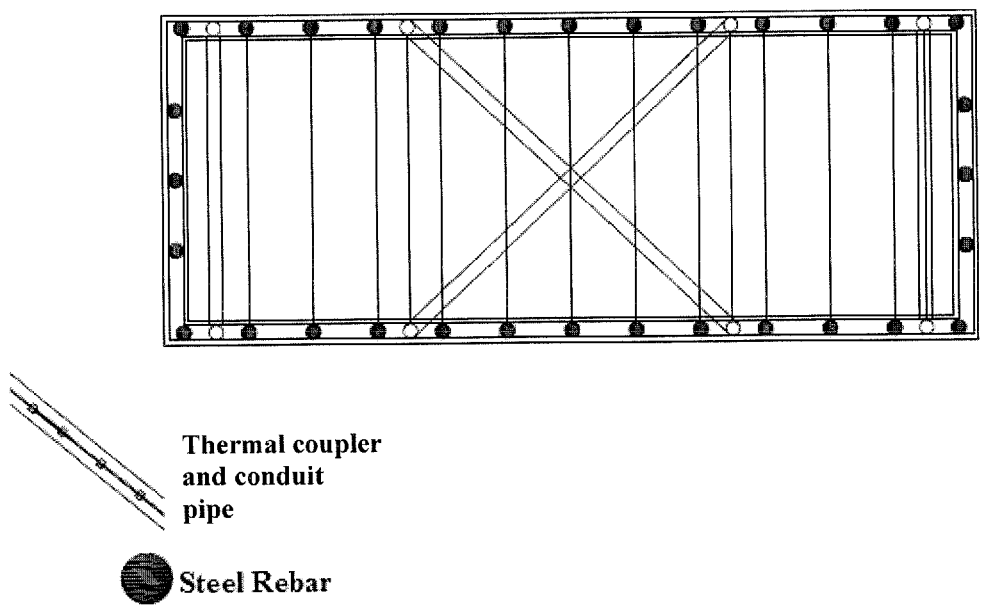
FIG. 6 shows an end view of the embodiment of FIG. 5.
Figure 7:
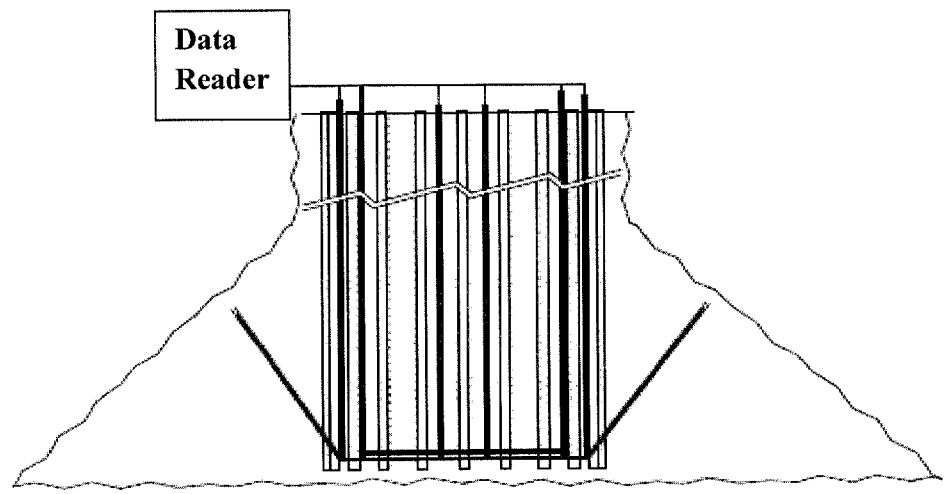
FIG. 7 shows a side view of a cylindrically shaped volume, where the concrete is not shown, showing conduit pipes with thermal coupler(s) within the conduit pipes, steel rebar, and a data reader.
Figure 8:
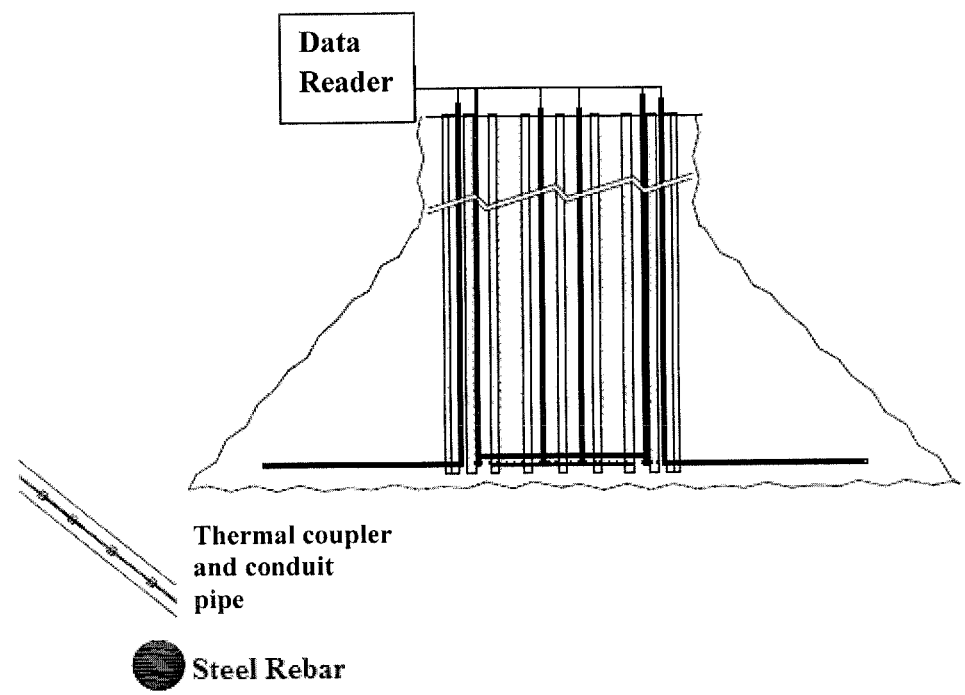
FIG. 8 shows a side view of a cylindrically shaped volume, where the concrete is not shown, showing conduit pipes with thermal coupler(s) within the conduit pipes, steel rebar, and a data reader.
Figure 9:
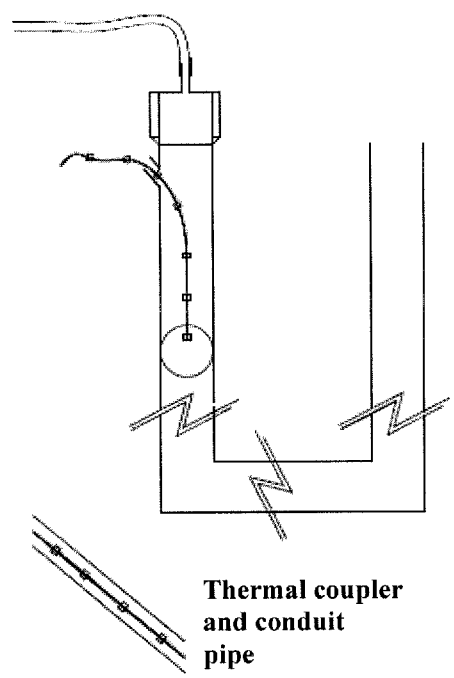
FIGS. 9 and 10 show a string being positioned by blowing.
Figure 10:
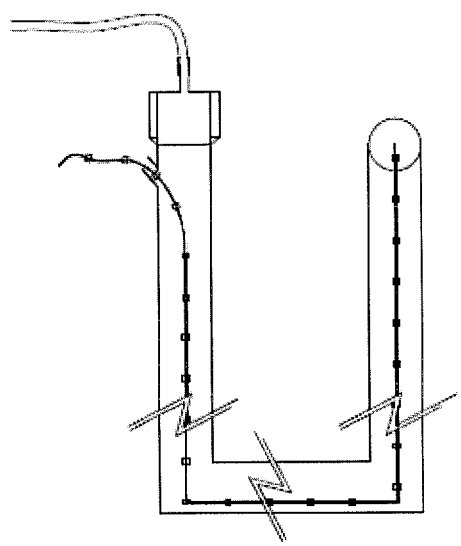
Figures 11, 12:
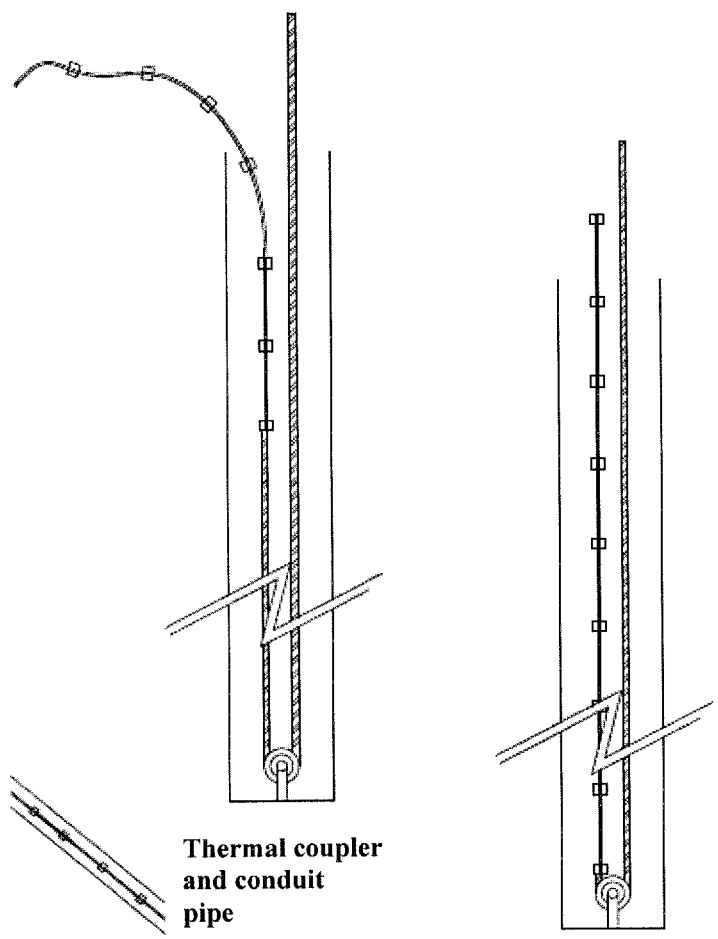
FIGS. 11 and 12 show a string being positioned by pulling.
Figure 13:
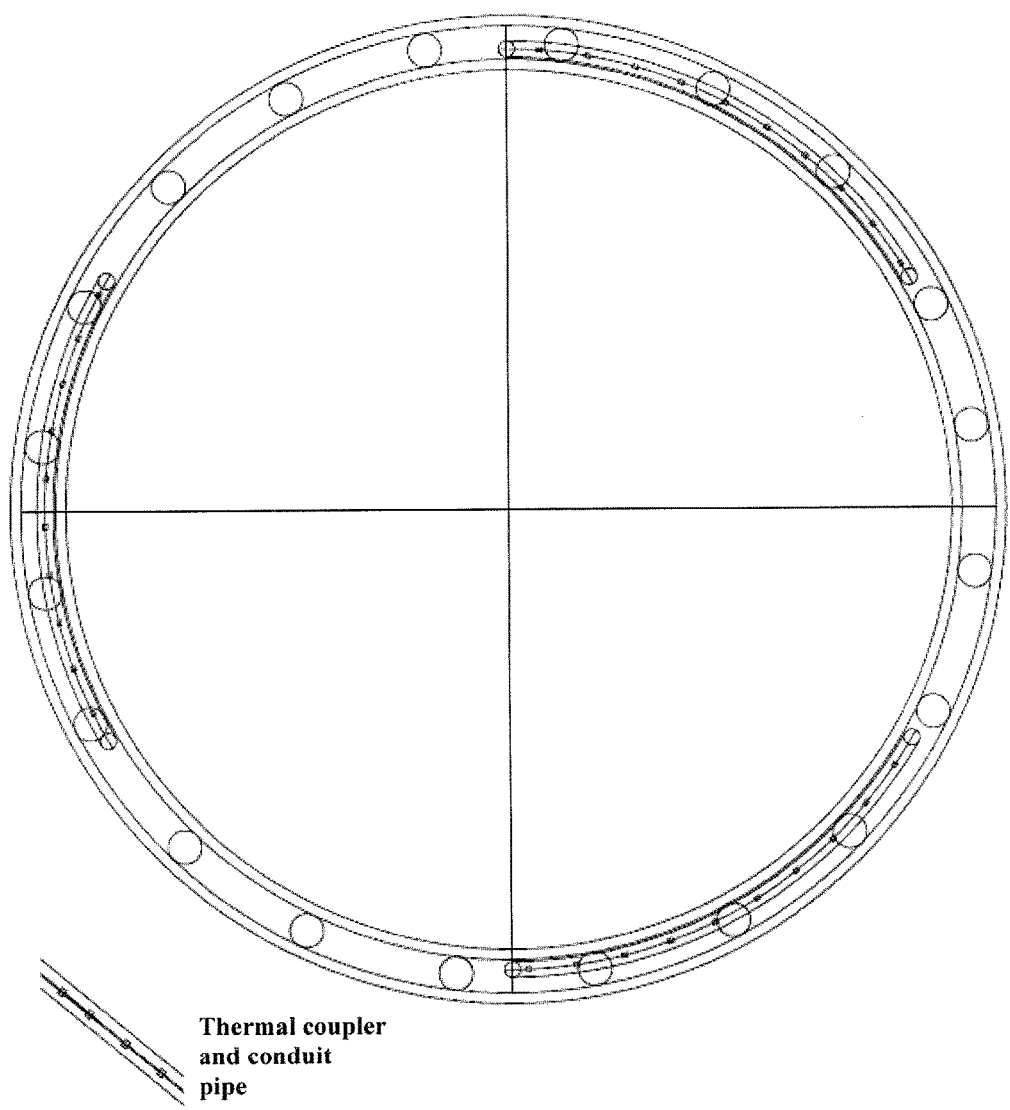
FIG. 13 shows an end view of an embodiment having a circular cross-section through the longitudinal axis where the conduits go down, follow the reinforcement structure, and come back up.
Figure 14:
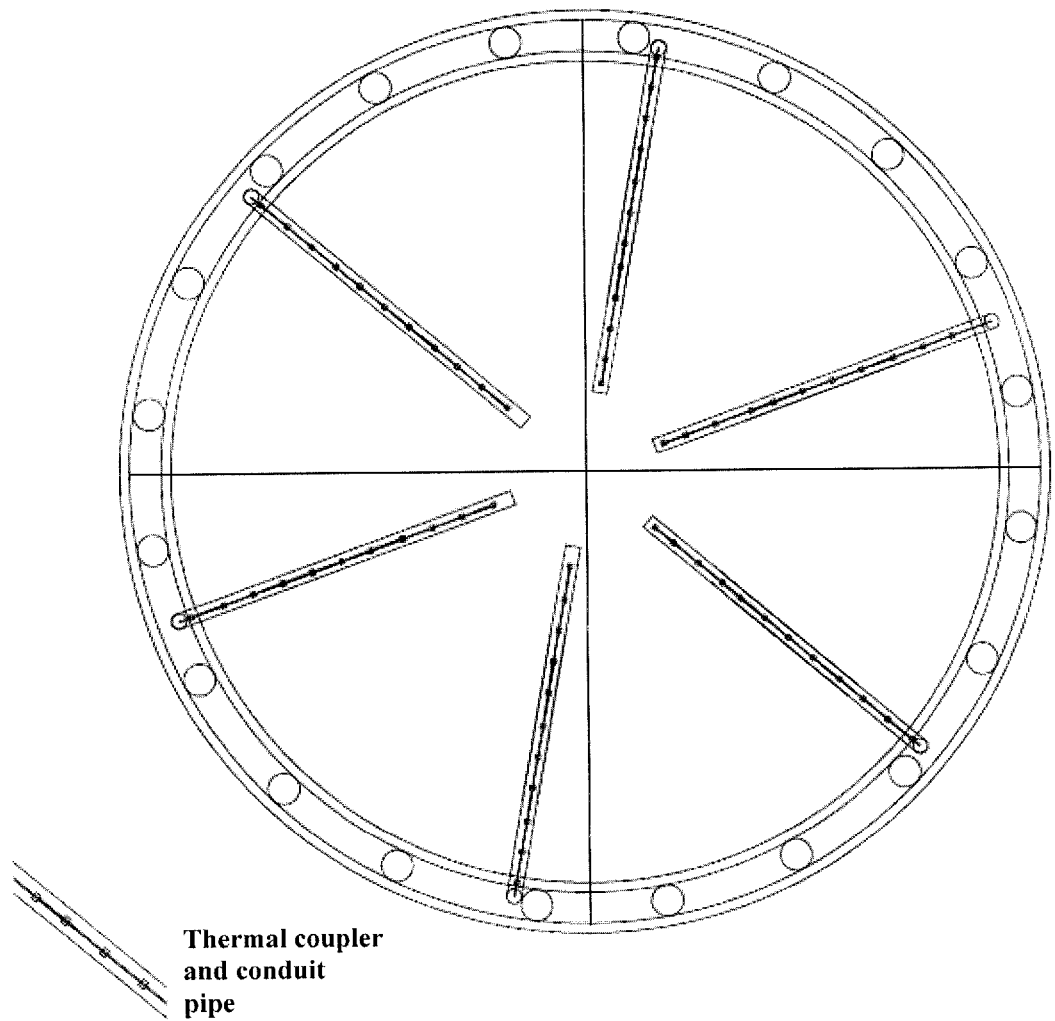
FIG. 14 shows an end view of an embodiment having a circular cross-section through the longitudinal axis where the conduits go down and extend towards the interior.
Figure 15:
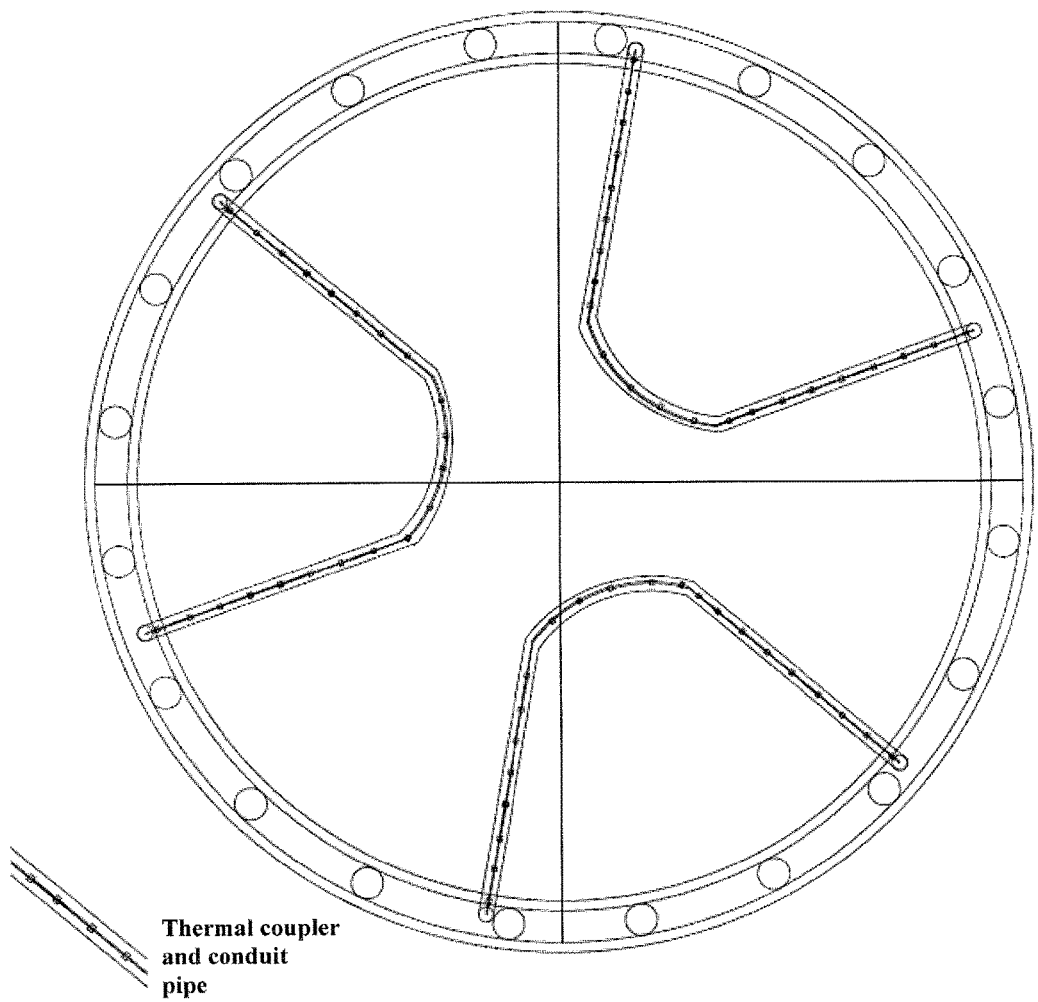
FIG. 15 shows an end view of an embodiment having a circular cross-section through the longitudinal axis where the conduits go down, extend out into the interior, and come back up.
Figure 16:
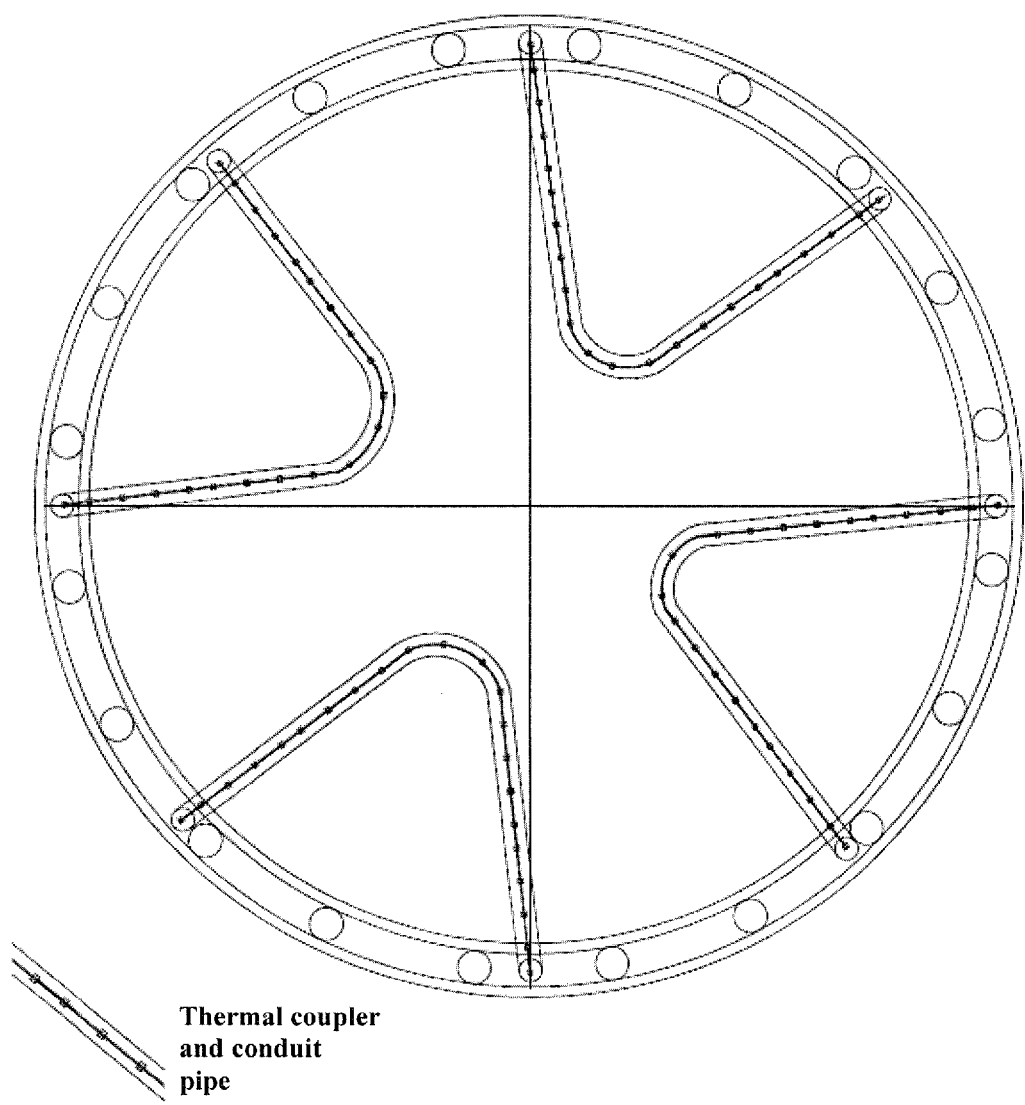
FIG. 16 shows an end view of an embodiment having a circular cross-section through the longitudinal axis where the conduits go down, extend out into the interior, and come back up.
Figure 17:
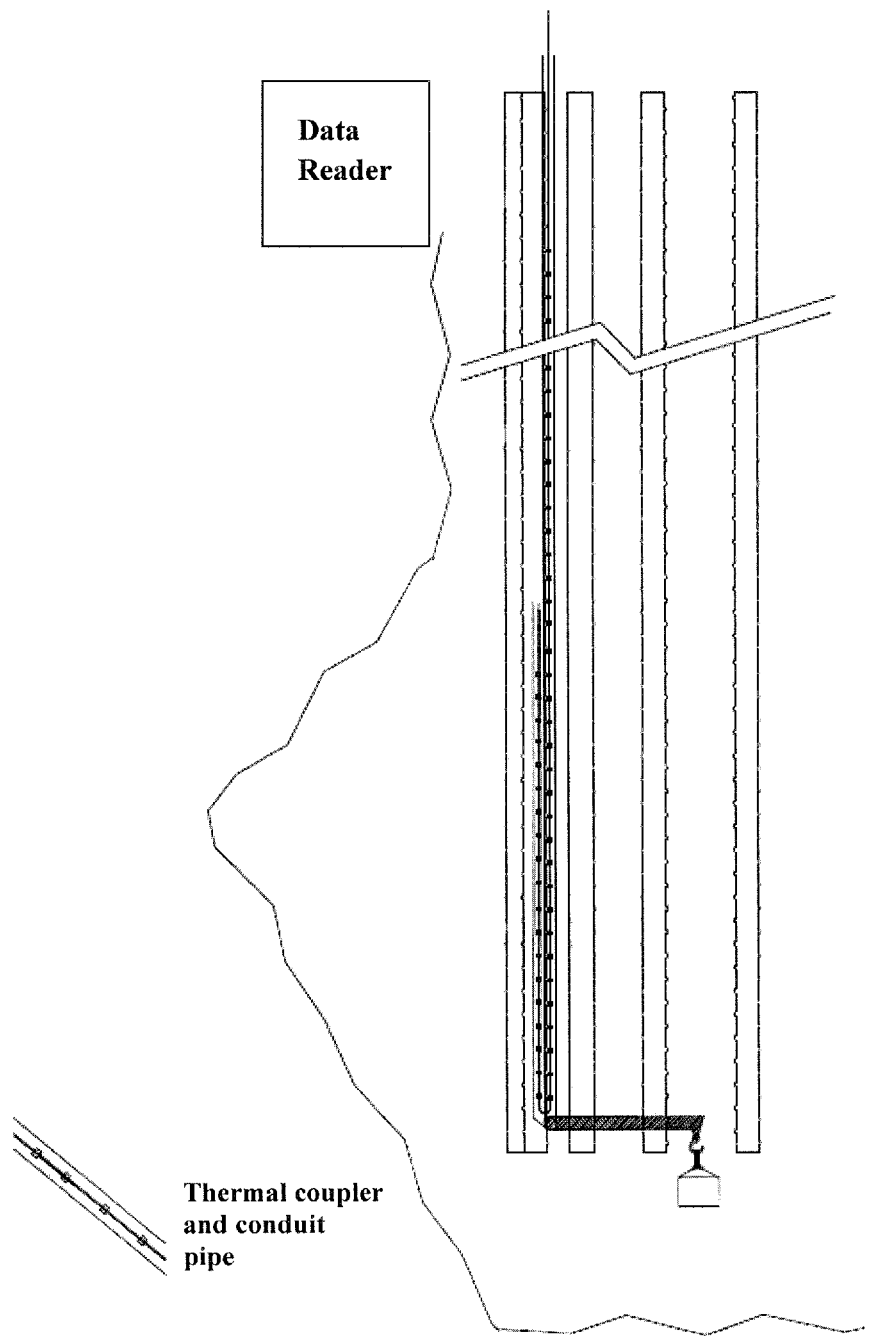
FIGS. 17-18 show an embodiment that allows the string to extend out into a void outside of the reinforcing cage.
Figure 18:
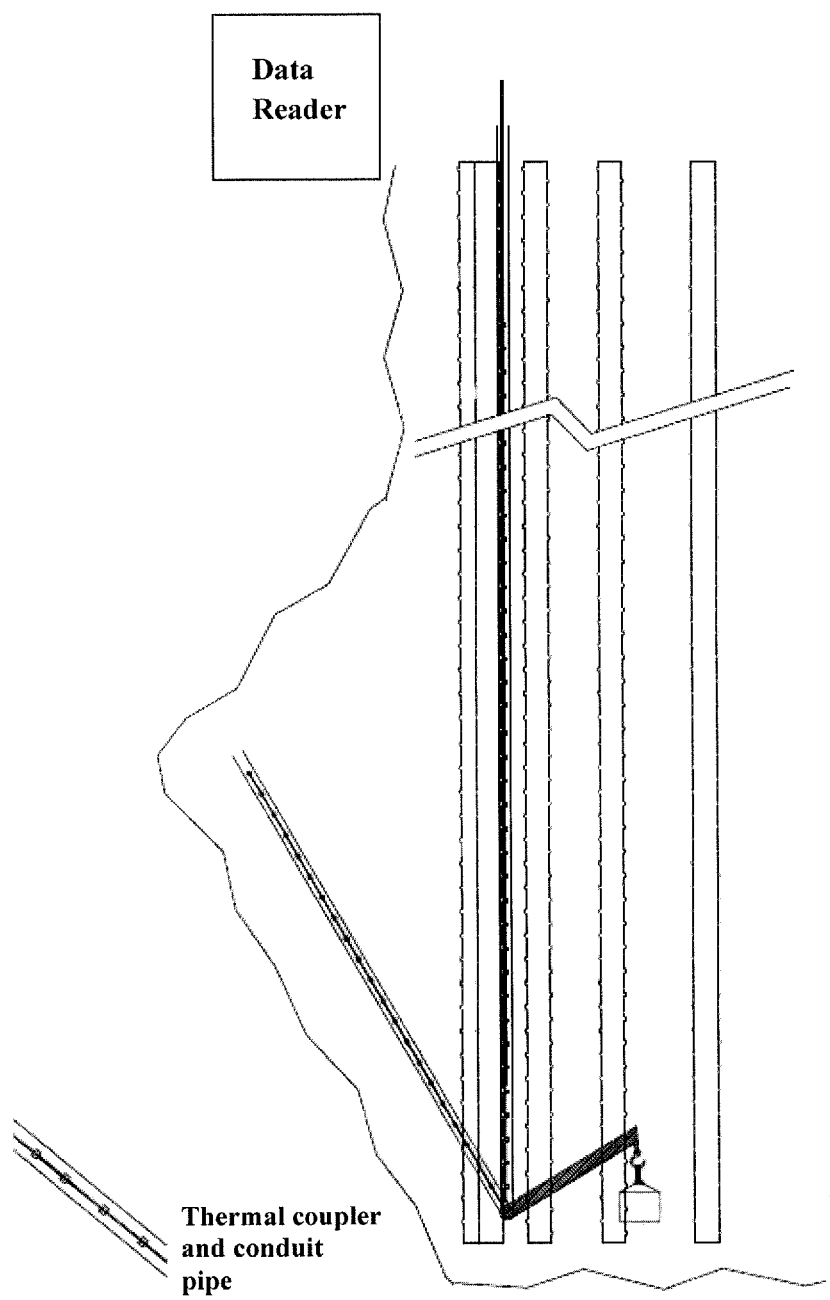
Figure 19:
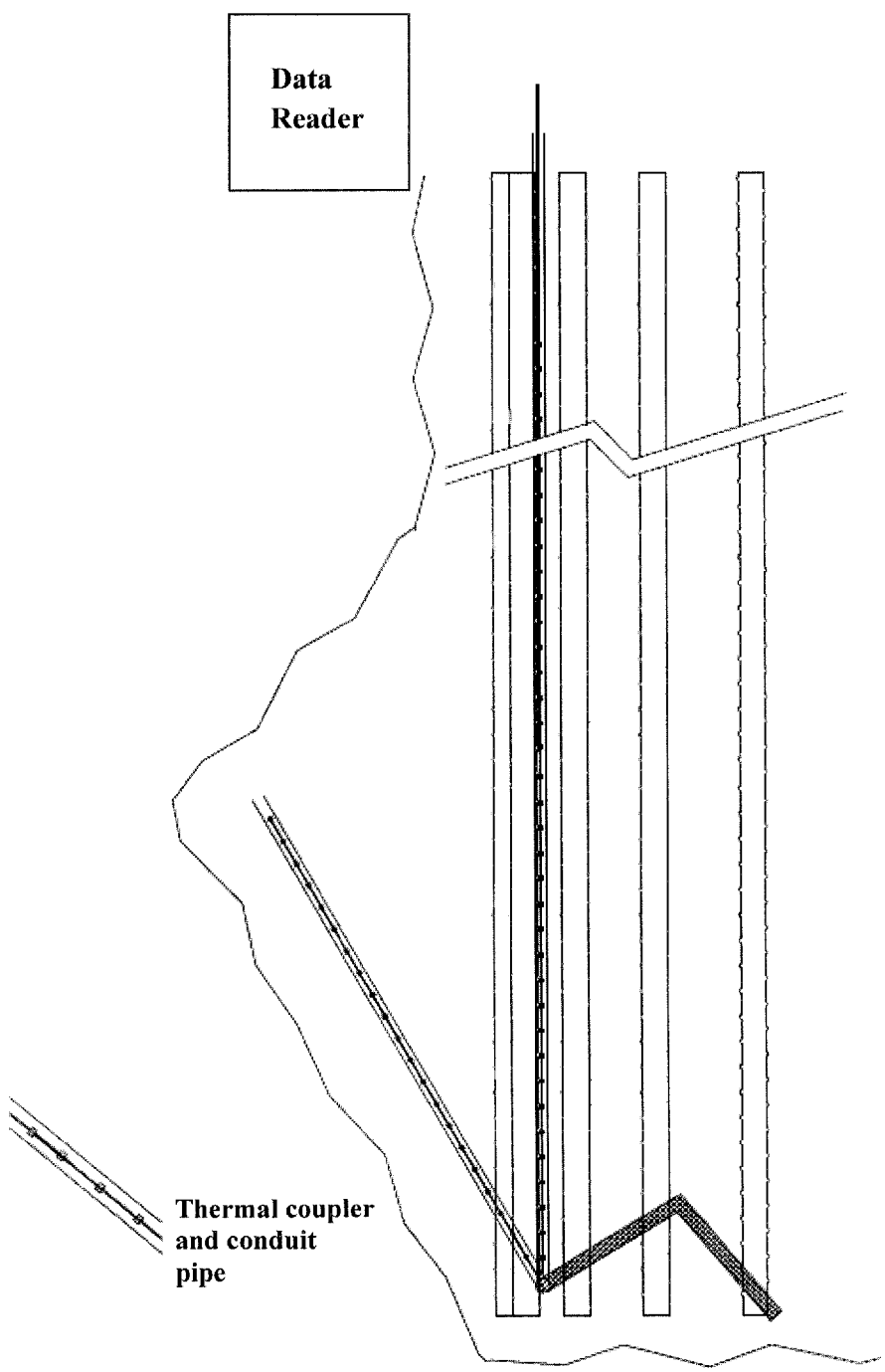
FIGS. 19-20 show an embodiment that allows the string to extend out into a void outside of the reinforcing cage.
Figure 20:
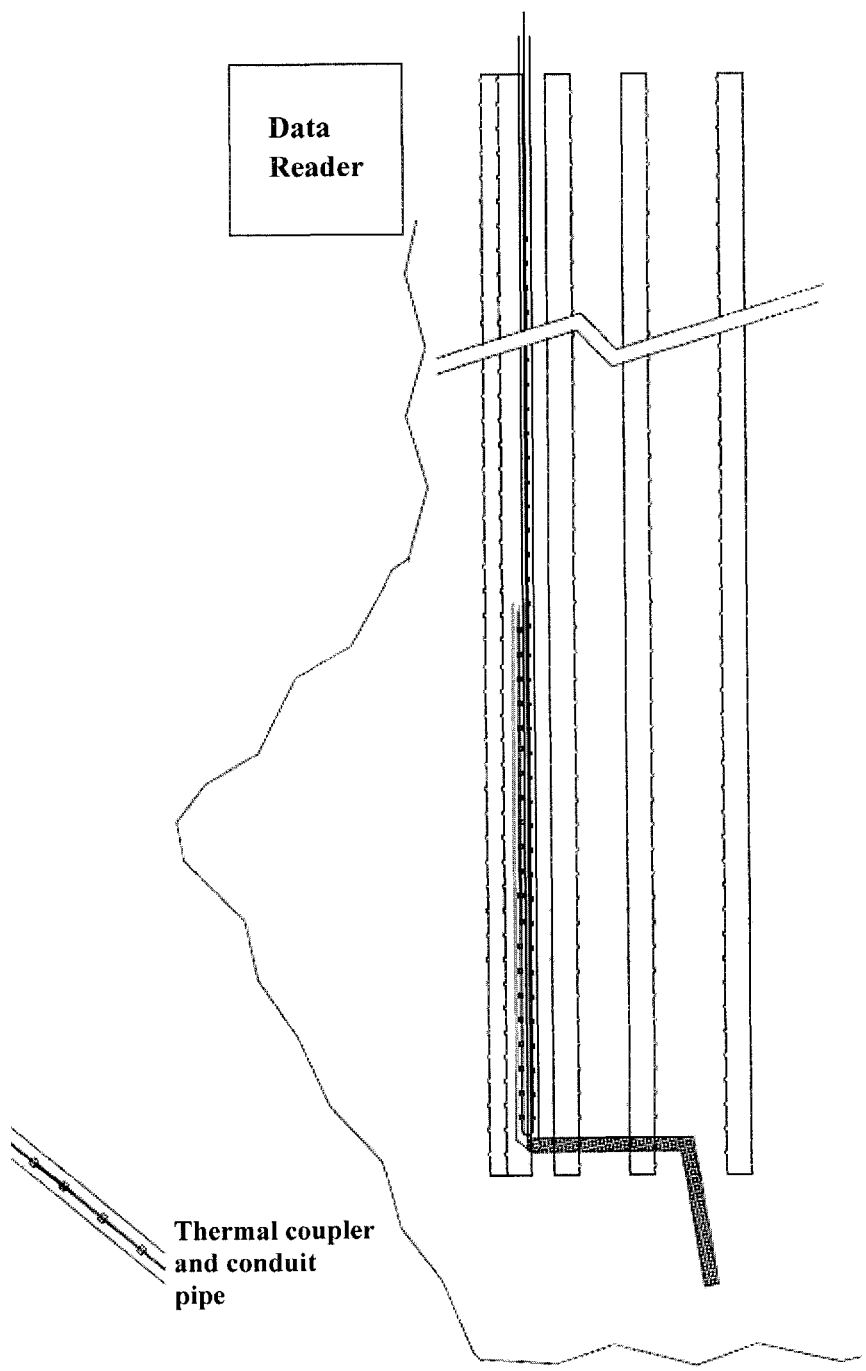
Figure 21:
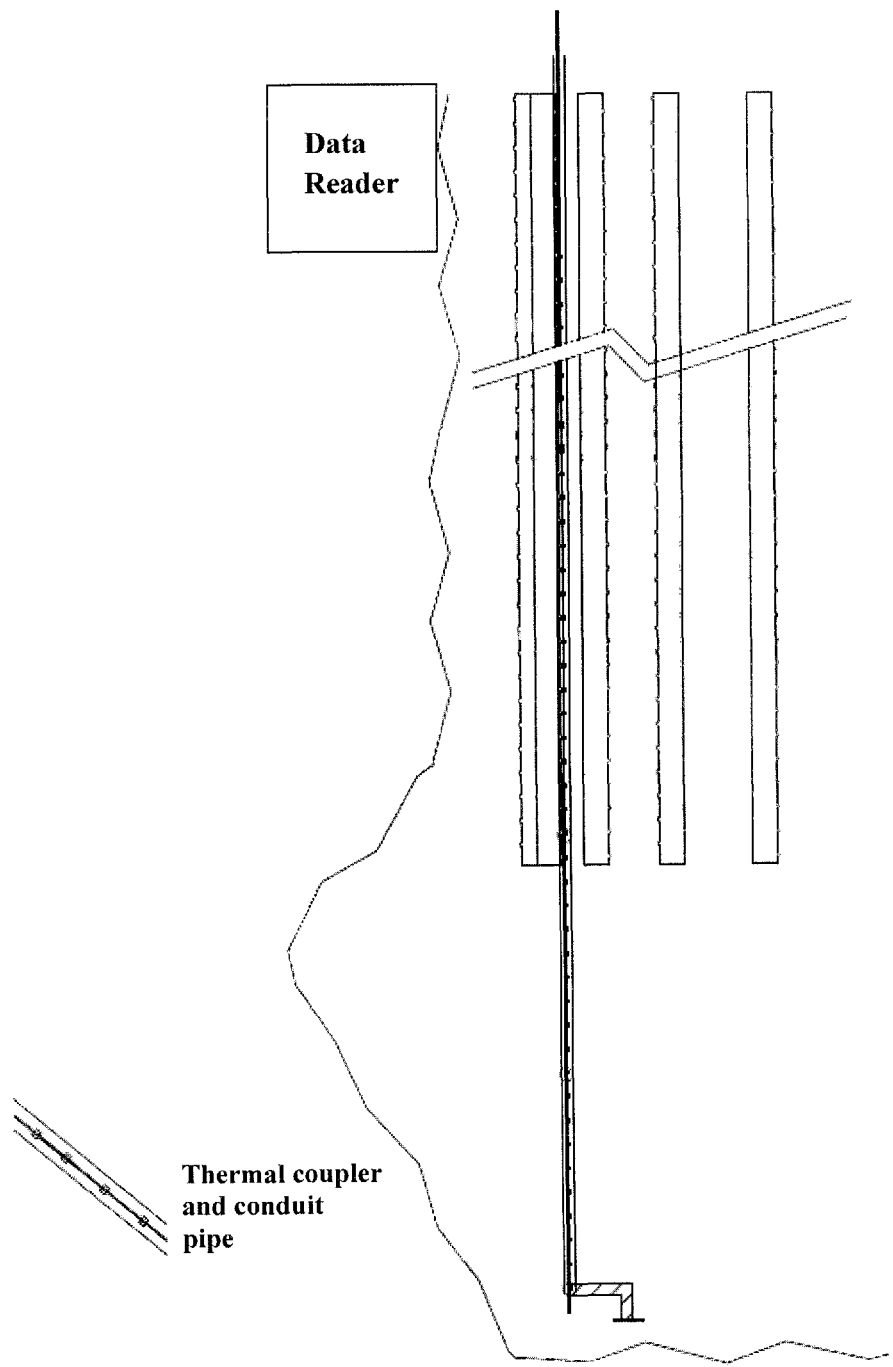
FIGS. 21-22 show an embodiment that allows the string to extend out into a void outside of the reinforcing cage.
Figure 22:
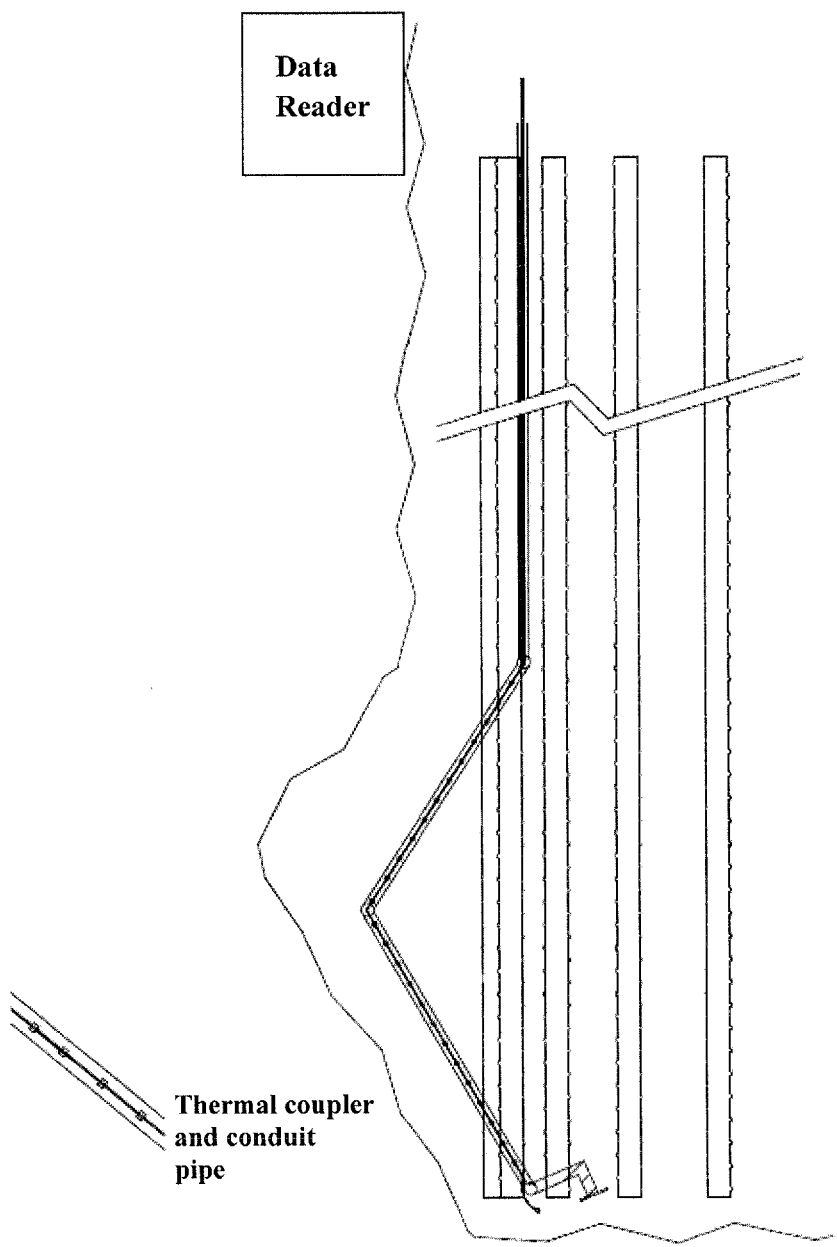

The conduits may be arranged on a typical reinforcing cylindrical (e.g., FIGS. 1 and 2) or rectangular (e.g., FIGS. 3 and 4) cage on the outside, inside, or within the perimeter. The conduits may be positioned, for example parallel to the axis of the foundation structure, in sufficient quantity to give full coverage of the perimeter or cross section. The conduit may also be arranged in a helical arrangement, such as within a spiral and/or helical tube positioned along the reinforcing cage downwards, thus providing a single continuous thermal string covering the entire perimeter or cross section.

For smaller cross sections, it may be convenient to insert a single steel reinforcing bar and/or conduit with a retrievable string down the center of the foundation element.

The retrievable strings may be placed in conduits by several techniques, including, but not limited to, the following:
1. self weight, using gravity to aid insertion (generally for vertical applications) and fed via the top of the conduit, it may be aided by pushing the string into the top of the conduit;
2. the use of a weight attached to one end of the string to allow gravity to pull the string into position;
3. by pulling with a leader string,
4. pushed through by rod or other mechanical structure, or
5. blown through the conduit with air or fluid before, during, or after concrete and/or grout placement (particularly appropriate for installation in two conduits where a circuit back to the surface is formed), and the string can be coaxed along the length of the conduit, or with the use of a pig, and/or pull the thermal string along the conduit.

Embodiments can use expendable conduits, as the conduits remain in the concrete after testing. The material for the expendable conduits (tubular, rectangular section, or other shape) may be plastic, steel, or other material and may be either dry or filled with a fluid. The conduit may be any shape providing the thermal string can be placed and removed from its interior. These conduits may either be placed specifically for temperature profiling purposes or be installed as part of a broader foundation program for either testing purposes, geothermal use, or any other requirement for conduits to be placed within the foundation element.
1. Tubes are often placed in the foundation element reinforcement for measurement of movements as part of a testing program (mechanical extensometers also called telltales), either for top down traditional static load testing or as part of the instrumentation required for bi-directional static load testing (telltale casing) to measure compression of the structure under load. These are generally of standard lengths and may be cut to size or extended using multiple lengths and couplers and sealed (except at the top);
2. Geothermal tubing—these are often used to exchange heat between the building and the foundations by circulating fluid through a heat exchanger. Several circuits or loops of semi-flexible pipe are attached to the reinforcing cage and inserted into the bore to nominal full depth of the foundation and then concreted into place with coupling at the top of the circuit to be integrated once the building is sufficiently advanced toward completion.
3. Base or shaft grouting pipework. Circuits with rigid and flexible pipes may be used to transmit pressurised grout to the bottom or side of the pile/foundation so that it may emerge from the pipe at desired preplanned locations to increase the lateral/downward pressure exerted on the virgin or disturbed soils surrounding the concrete. The grouting procedure is normally performed some days after concrete casting, which may be 2-10 days, allowing time for the grout access pipework to be used to house retrievable thermal strings prior to their normal application.
4. A specifically designed and installed conduit for the purposes of the thermal profiling, several arrangements may be used as described in 7 and 8 below.
5. Some of the steel vertical reinforcing bars can be hollow or replaced with steel tubing during cage manufacture so the steel of the conduit doubles as part of the steel reinforcement required. A helical steel can be used as a hollow conduit.
6. Installation of some ground anchors or minipiles require insertion of a hollow tube into the excavation through which grout is pumped in a manner where its flow emerges from the extremity of the tool at the bottom of the bore. Sometimes the tool is expendable, and a conduit can be inserted in the hollow. If retrievable, the expendable conduit can be attached to the nose of the tool so it stays in place after grouting. Some anchors may have a single reinforcing bar inserted in the wet grout, to which the conduit may be attached for full insertion into the wet grout.
7. Pre-prepared lengths of conduit may be used where the retrievable thermal string is pre-installed in the conduit prior to placement in the shaft/bore.
   a. With a sealed base with a pre-installed retrievable thermal string. The conduit is left embedded within the structure element whilst the thermal string can be removed/extricated after the concrete/grout has hardened.
   b. With a pre-installed thermal string that may be joined together by means of connectors prior to the installation of the reinforcement and at the splice on installation. Electrical connection and/or mechanical connection of the conduit can also be implemented;
   c. With lengths longer than the foundation elements reinforcing cages, with a pre-installed and retrievable thermal string, that is attached to the outside of the reinforcement cage as the cage is lowered into the excavation.
   d. With pre-installed retrievable strings that can be pushed into the top of the concrete of a cast in situ foundation element, a soil mix-in-place or grout injection column after the column has been formed. These may be directly attached to reinforcing cages intended to be plunged into concrete or grout (such as with continuous flight auger piles)

Conduit and pre-installed thermal string may also be prefilled with heat conducting fluid, water, oil, and/or grease before the concreting phase commences thus reducing ingress of grout/concrete into the conduit that would prevent the string's post-test removal.

Embodiments can use conduit as described above positioned at least partially within the concrete, and additional conduit placed at the base to allow the thermal profile of the base to be assessed, where the additional conduit is placed at one or more of the following:

Around the periphery of the foundation element base, outside of the reinforcing cage;

Around the perimeter of the reinforcing cage, following and mounted on the reinforcing cage ring at the base;

Across sections of the foundation element base secant sections, either straight or circular;

Across the center of the foundation element base, following the radius to the center or close to the center and then returning to either a second conduit at some angular position on the reinforcing cage or diametrically opposite the first.

8. U-tube, twin or multiple conduit arrangements joined at the base with a substantially U shaped connection. Parallel conduits can be placed around the reinforcing cage or arranged inside and outside the perimeter of the reinforcing cage. In an alternative embodiment, the use of a continuous tube U-shaped conduit or as part of geothermal circuits cast in the concrete, allows fluid of a different temperature (hotter or colder) to be circulated to change the local temperature of the surrounding concrete either with the retrievable thermal string already fitted or fitted subsequently, so that the decay of temperature back to the ambient (surrounding soil) can be monitored. An application which can therefore be applied retrospectively to cast foundation elements.

9. The conduit for the removable thermal string can be made to extend beyond the envelope of the reinforcing cage after insertion in the bore so that they may penetrate into an additional excavation that would form an under-ream or ream. Assessment of the concrete structure in this zone has not previously been possible. The construction of ream and under-reams may require additional tools to be inserted into the straight bore as it is being constructed to produce a further boring (generally of circular geometry) making the additional excavation up to 5 times the diameter of the straight shafted bore. Reinforcing cages are commonly used for the full length and the semi-rigid or flexible conduit for the removable thermal string may be attached to the outside of the reinforcing cage and by mechanical operation some or all of the strings may be made to extend into the ream or under-ream onto the upper or lower surface of the reamed excavation.

To achieve improved pile capacity without the need for additional foundation element depth, a large diameter drilled shaft may benefit by having a ream or an under-ream formed. A ream is defined as an over-bored diameter by means of a tool which extend the sides of the shaft outwards beyond the cylindrical envelope. An under-ream uses a tool to make an enlarged base of the shaft by increasing the base of the shaft to form a bell or cone shape. Reams and under-reams do not normally contain reinforcement and just filled with concrete but are subject to collapse during forming. The removal of debris from the base of the ream/under-ream is extremely difficult with a variety of method and complicated tools being designed to provide greater efficient with the formation and cleaning the base of the ream. Often cameras are used to determine the shape of the ream/under-ream and the existence of any debris before the main reinforcement is placed.

Placement of thermal strings within the ream section can assist in the determination of the shape of the ream and the extent to which the base of the ream was cleaned of debris before concreting.

Positioning of thermal strings in a ream or under-ream requires their deployment outside of the reinforcement cage after it has been placed in the bore by mechanical means. This can take the form of hinged sections connected either at the base of the reinforcement cage corresponding to the bottom of the ream so that the additional thermal conduits can be located on or near the bottom of the ream.

Sections of the thermal string conduits, connected to steel bars hinged at the reinforcement cage may be arranged so that on final descent of the cage reaching the bottom of the bore, the bars can connect with the base material and cause the arms to move in a manner that deploys the conduit outwards. Alternatively, the sections can be held in place with a rope or string during installation of the cage and released once the cage is in the correct position. To position the thermal strings in the upper section of the ream or under-ream excavation, the hinge is placed on the reinforcing cage at an elevation which corresponds to the elevation of the top of the ream section. To release the hinged section, a rope connected to the top of the reinforcement cage may be released or pulled according to the configuration so that the conduit arms are released.

The successful construction of the base of a foundation element, whether it be a piled shaft or a wall/barrette type excavation, has always been difficult assess with respect to:
a. the integrity of the concrete/grout material placed at the base;
b. the presence of any debris or contaminated material at the base, either from the excavation soils or settlement from the drilling fluids;
c. the soils forming the base of the foundation;
d. the effectiveness of base grouting.

As a result, for some foundation element designs, the contribution from the end bearing is deliberately ignored as there are no test procedures, other than full scale loading, which can allow the base behaviour and suitability to be evaluated, but because of its high cost would not be carried out on all foundation elements.

During excavation of the foundation element, a cutting tool of some form is used (with the exception of driven or soil displacement piles). The shape and nature of the cutting tool/s will determine both the shape of the excavation and together with the type of soils being bored, affect the likelihood of debris or loose material being left behind after tool removal. The ideal base that might be formed would be clean, free of all debris and one in which the concrete of the foundation element engages directly with the virgin soil beneath. However, often, once the excavation has taken place, the soil at the base of the excavation may heave in time, softening the material and reducing the effective bearing capacity in terms of stiffness.

Excavation by hydrofaise or grab in a rectangular section excavation will leave behind material at the edges of the base of the excavation and in the case of the hydrofraise, the area of soil between the cutting wheels at the center.

At depth, and under drilling fluid, it is extremely hard to determine the shape of the base and the presence of debris. In addition, particles from the drilled soil get stirred up into the drilling fluid and get held in suspension or sinking to the base of the excavation by sedimentation to form a layer of soft material. Air lifting and cleaning of the supporting fluid by recirculation and desanding can reduce the particle content and therefore the material that may get deposited onto the base.

Where the concrete is placed by tremie pipe, it is often considered that the majority of any debris at the base of the excavation will be swept up the shaft removing it from the base and have some scouring effect. However, the effectiveness of the procedure is not known and debris can often be caught up at the edges of the base thus reducing the effective diameter of the end bearing component of the foundation element.

Base grouting is often recommended as a possible remedial step to poor installation of the base foundation element and in an attempt to improve the load/settlement characteristics of the pile. But there are no testing methods that can reveal the effectiveness of the base construction before executing the costly procedure of base grouting.

A method of determining, the effective shape of the base, the presence of debris at the base and whether base grouting could be effective would, therefore be an invaluable tool to both the engineer and designer.

By placement of a retrievable thermal string, not only along the shaft of the foundation element, but at the point at which the difficulties of shape determination and quality of concrete/grout are experienced, a profile of the base of the shaft can be determined and the presence of anomalies in the concrete/grout quality can be assessed.

Since the thermal properties of the surrounding materials is known, it will be possible to use the temperature profile and response at the base of the excavation to infer the type of material surrounding the base, and whether the natural material has been disturbed to an extent to adversely affect the bearing capacity.

In a further embodiment, the retrievable thermal string in a foundation element, will allow measurement of the temperature change due to the injection of grout at the base or along the shaft; a procedure performed after concreting in some soils in an attempt to improve the skin friction (side shear) and foundation element behaviour.

The placement of the retrievable string methods can be further described:
I. A thermal string may be pushed down a single access conduit using a leader attachment on the end of a rigid or semi-rigid rod to enable the string to be pushed down the conduit from the top by the rod. The rod may then;
   a. Remain in place during the duration of testing. The same rod can then be used to assist in the withdrawal of the string.
   b. Be removed once the string is in place. The string will then be pulled out after testing.
II. A thermal string may be pulled down a single conduit by means of a lead string or wire which is preinstalled so that the string or wire loops through an attachment at the bottom end of the conduit with both ends of the string or wire being at the top of the conduit. One end of the lead string or wire is attached to the thermal string while the other end is pulled out of the conduit. This action draws the thermal string down the conduit until it stops at the bottom of the conduit. At end of test the thermal string is pulled back out of the conduit from the top.
III. A thermal string may be placed in a conduit by means of a weighted end attached to the bottom of the thermal string. The thermal string is then placed by gravity into the conduit and removed by pulling out from the top after testing.
IV. A thermal string may be placed in a twin conduit which is connected at the bottom of the foundation element to allow the passage of the thermal string to pass from one conduit to the other. The string may be placed by;
   a. Pulling with a lead string preplaced within the conduits in the path that the thermal string will be required to follow. The thermal string may be pulled through more than one pair of conduits to make a continuous thermal string within multiple conduits.
   b. Pulling with a lead string placed within the conduits, prior to concreting, in the path that the thermal string will be required to follow. The string may be placed by pushing the string by means of a 'pig' that is pushed by air or fluid flow through the conduit path. The air or liquid fluid may be pumped under pressure so that the fluid passes along the conduit paths from top to bottom. The leader string may then be used to draw the thermal string along the conduit.
   c. A 'pig' may be attached to the string directly which is drawn along behind the conduit. The thermal string may be pulled through more than one or more than a pair of conduits to make a continuous thermal string within multiple conduits.
   d. The thermal string may be constructed in a semi-rigid form so that it may be pushed from the top along the conduit path until it reaches the top of the second conduit. This may be in the form of a continuous semi-rigid cable or the form of articulated rigid sections connected together to make a semi-rigid system.

Where an optical fiber optic sensor is used that also has strain measurement capabilities, the string may be grouted in place prior to load testing. The string would then become sacrificial and irretrievable.

The use of small diameter tubes or conduit allows a cost effective solution for structural elements not normally fitted with CHSL tubes such as continuous flight auger (CFA)/auger cast, driven cast in situ, grout injection columns and driven cast in situ piles being an example of just a few types.

Monitoring may be made by use of either a singular display measurement unit connected to each sensor individually or a number of sensors may be read by a single data logger, where the strings are set in series, or by multiple data loggers attached to individual strings, the data being collated after monitoring for analysis and display. In a preferred embodiment, a series of thermal sensors (MEMS) type devices are all connected in series and the logger unit addresses each one with a digital address and logs its response—in this manner several thousand devices can be arranged to respond to their unique address and be polled in turn to get the temperature response from each in succession.

In a secondary application of the retrievable thermal strings, as they may have been located in the conduit prior to concrete placement, they may be used as an aide to assist in the concrete pouring progress as well as pour profiling. By monitoring the temperature change along any thermal string, the level of concrete within a bore or casting can be assessed as the concrete is being poured if the temperature between the air or drilling fluid is just slightly different to that of the concrete and detectable. Rising levels of concrete will change the temperature along the string allowing the location of the concrete and more importantly the top of the concrete as it rises up the shaft to be assessed. When taken in conjunction with the volume of concrete placed, an assessment can be made of the general profile of the foundation element and assist in the calculation of the required overall concrete volume without the need to use crude and time consuming 'dipping' techniques which involve weighted tape measures or other similar devices lowered down the excavation until the dense concrete is detected, which is a common procedure used to assess the level of concrete as it rises up the excavation. Where bi-directional jacks or other obstructions have been placed across or within the excavation, such 'dipping' techniques may be impractical as bearing plates, jacks or other cross-hole devices may block the path of the measuring tape or wire. A thermal string with temperature monitoring sensors with known spacing may be monitored continuously as the concrete is poured giving a live indication.

Temperature of concrete during its curing can be monitored manually by thermometers or automatically by use of thermocouples connected to a data acquisition system. The preferred temperature sensors are thermocouples, which is a temperature sensor formed by connecting two wires of dissimilar metals. A temperature gradient between the ends of the wires generates a small DC voltage which is directly proportional to temperature. The sensitivity available depends on the materials used to make the thermocouples.

The individual sensors monitoring the concrete level during the pour may be read either by:

a. A hand held device monitoring one sensor at a time. Monitoring may start at the bottommost sensor. Once the temperature has changed at a specific sensor, the monitoring system is connected to the adjacent higher sensor, the level of the concrete having been established as being between these two elevations. This single sensor monitoring is continued while tracking the top of the fluid concrete until the concrete has reached the desired level.
b. By use of a data logger or other computerised/automated monitoring device. Suitable dataloggers are those supplied by Campbell Scientific such as the CR1000 or from DataTaker such as the DT500 or 600 series. The data is recorded and concrete pour data recorded manually or input directly into a computer. The sensor readings may then be either, shown on site as real time data, plotted to show concreting progress or stored for future analysis, or a combination of all three.
c. The sensors may be connected to a visual display system where the progress of the concrete pour may be visually displayed due to temperature change at the sensor level. This visual display may then be used as an aid to assist in the determination of the concrete level and to assess the concrete volume requirements of the concrete pour.

The placement of strain gauges, which may also contain a thermal sensor, within the reinforcement cage at discrete levels, may be considered to be a thermal string and may be used in a similar manner as the thermal strings described above.

Specific embodiments can incorporate temperature sensors such as RST Instruments thermometer string assemblies EL3800025, EL 380004, EL380005, EL 380008, EL 380012C, EL 380013P, and EL 380026.

Specific embodiments can incorporate an RST Instruments Digital Therm Array system, and/or an RST flex DAQ Data logger system, a laptop or a PC.

Aspects of the invention may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, and numerous details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention may be practiced without these specific details. Computer systems, servers, work stations, and other machines may be connected to one another across a communication medium including, for example, a network or networks.

As one skilled in the art will appreciate, embodiments of the present invention may be embodied as, among other things: a method, system, or computer-program product. Accordingly, the embodiments may take the form of a hardware embodiment, a software embodiment, or an embodiment combining software and hardware. In an embodiment, the present invention takes the form of a computer-program product that includes computer-useable instructions embodied on one or more computer-readable media.

Computer-readable media include both volatile and non-volatile media, transitory and non-transitory, transient and non-transient media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile disks (DVD), holographic media or other optical disk storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A method for investigating the uniformity of concrete, comprising:
   placing one or more access bores at least partially within concrete positioned in a volume and/or proximate the concrete positioned in the volume,
   wherein the one or more access bores comprise one or more access tubes, and
   wherein at least one access tube of the one or more access tubes is placed such that a corresponding at least one longitudinal axis of the at least one access tube of the one or more access tubes is across a base of the concrete positioned in the volume;
   positioning a string within the one or more access tubes, wherein the string comprises at least two temperature measuring sensors;
   collecting temperature data from the at least two temperature measuring sensors; and
   retrieving the string from the one or more access tubes.

2. The method according to claim 1, wherein at least one access tube of the one or more access tubes is attached to a reinforcement cage or framework placed within the concrete.

3. The method according to claim 1, wherein at least one access tube of the one or more access tubes is cast in place before concrete positioned in the volume.

4. The method according to claim 1, wherein at least one access tube of the one or more access tubes is plunged in the concrete positioned in the volume before the concrete cures.

5. The method according to claim 1, further comprising: processing the temperature data to produce a 3D representation of temperature variations in the concrete.

6. The method according to claim 1, further comprising: processing the temperature data to identify an existence of an anomaly in the uniformity of the concrete.

7. The method according to claim 1, further comprising: processing the temperature data to determine a size of an anomaly in the uniformity of the concrete.

8. The method according to claim 1, further comprising: processing the temperature data to determine a location of an anomaly in the uniformity of the concrete.

9. The method according to claim 1, further comprising: processing the temperature data to determine a type of an anomaly in the uniformity of the concrete.

10. The method according to claim 1, further comprising: processing the temperature data to determine a shape of an anomaly in the uniformity of the concrete.

11. The method according to claim 1, wherein the concrete forms a foundation element after curing.

12. The method according to claim 1, wherein the one or more access tubes comprise one or more telltale casings in the concrete, and wherein the string is positioned within the one or more telltale casings during at least a portion of the time the concrete is curing.

13. The method according to claim 12, further comprising: wherein after the string is retrieved from the one or more telltale casings, the one or more telltale casings are used for load testing.

14. The method according to claim 13, wherein at least one telltale casing of the one or more telltale casings has an inner diameter of 12 mm to 18 mm.

15. The method according to claim 1, wherein the concrete positioned in the volume is a cast in pile after curing, wherein the method further comprises: monitoring a level of concrete positioned in the volume during construction of the cast in pile.

16. The method according to claim 1, wherein the concrete positioned in the volume has a circular cross-section through a longitudinal axis and a diameter less than 2 meters.

17. The method according to claim 16, wherein the concrete positioned in the volume has a diameter less than 1 meter.

18. The method according to claim 1, wherein the concrete positioned in the volume has a rectangular cross-section through a longitudinal axis, and wherein a width of each side of four sides of the concrete positioned in the volume is less than 2 meters.

19. The method according to claim 1, wherein the concrete positioned in the volume has a rectangular cross-section through a longitudinal axis, and wherein a width of each side of four sides of the concrete positioned in the volume is less than 1 meter.

20. The method according to claim 1, wherein the concrete positioned in the volume has a cross-sectional area through a longitudinal axis of less than $4\pi$ m$^2$.

21. The method according to claim 1, wherein the concrete has a cross-sectional area through a longitudinal axis of less than $\pi$m$^2$.

22. The method according to claim 1, wherein the string is flexible, semirigid, rigid, or segmented.

23. The method according to claim 1, wherein the string incorporates a continuous wire or continuous rope.

24. The method according to claim 1, wherein the string comprises at least 100 temperature measuring sensors.

25. The method according to claim 1, wherein at least one access tube of the one or more access tubes has a corresponding at least one inner diameter of less than 60 mm.

26. The method according to claim 1, wherein at least one access tube of the one or more access tubes is filled with fluid when positioning the string.

27. The method according to claim 1, wherein the string is positioned by pushing the string down a single access tube using a leader attachment on the end of a rigid or semi-rigid rod.

28. The method according to claim 1, wherein the string is positioned by pulling the string down a first access tube of the one or more access tubes by way of a lead string or wire which is preinstalled so that the lead string or wire loops through an attachment at a bottom end of the first access tube of the one or more access tubes with both ends of the lead string or wire being at a top end of the first access tube of the one or more access tubes, and wherein a first end of the lead string or wire is attached to a first end of the string while the second end of the lead string or wire is pulled out of the first access tube of the one or more access tubes, so as to draw the first end of the string down the first access tube of the one or more access tubes until the first end of the string stops at the bottom end of the first access tube of the one or more access tubes.

29. The method according to claim 28,
wherein after collecting temperature data from the at least two temperature measuring sensors, pulling the string out of the first access tube of the one or more access tubes from the top end of the first access tube of the one or more access tubes.

30. The method according to claim 1,
wherein the string has a weighted end attached to a bottom of the string, and
wherein the string is positioned within the first access tube of the one or more access tubes by gravity pulling the string into the first access tube of the one or more access tubes.

31. The method according to claim 30,
wherein retrieving the string comprises pulling the string out of the first access tube of the one or more access tubes from the top end of the first access tube of the one or more access tubes after collecting the temperature data.

32. The method according to claim 1,
wherein the string is positioned by placing the string in a twin pair of access tubes of the one or more access tubes which are connected at a bottom of the concrete positioned in the volume to allow passage of the string from a first access tube of the twin pair of access tubes to conduit a second access tube of the twin pair of access tubes.

33. The method according to claim 32,
wherein the string is placed by pulling the string with a lead string preplaced within the one or more access tubes in a path that the string will follow.

34. The method according to claim 1,
wherein the temperature data is monitored during curing of the concrete.

35. The method according to claim 1,
wherein at least one access tube of the one or more access tubes is geothermal tubing, and
wherein after the string is removed from the geothermal tubing, the geothermal tubing is used for geothermal heat exchange.

36. The method according to claim 1,
wherein at least one access tube of the one or more access tubes is base or shaft grouting pipework, and
wherein after the string is removed from the base or shaft grouting pipework, the base or shaft grouting pipework is used to transmit pressurized grout.

37. The method according to claim 1,
wherein at least one access tube of the one or more access tubes is a corresponding at least one hollow reinforcing bar.

38. The method according to claim 1,
wherein at least one access tube of the one or more access tubes is a corresponding at least one cross hole sonic logging tube, and
wherein after the string is retrieved from the at least one cross hole sonic logging tube, the at least one cross hole sonic logging tube is used for cross hole sonic logging.

39. The method according to claim 1,
wherein the string incorporates at least one strain gauge.

40. The method according to claim 1, further comprising:
a processor,
wherein the processor receives the temperature data and determines a concrete level in real time during pouring of the concrete.

* * * * *